United States Patent [19]
Will et al.

[11] Patent Number: 6,114,159
[45] Date of Patent: Sep. 5, 2000

[54] DNA SEQUENCES FOR MATRIX METALLOPROTEASES, THEIR PRODUCTION AND USE

[75] Inventors: Horst Will; Bernd Hinzmann, both of Berlin, Germany

[73] Assignee: Max-Delbrück-Centrum für Molekulare Medizin, Berlin, Germany

[21] Appl. No.: 08/704,711

[22] PCT Filed: Mar. 17, 1995

[86] PCT No.: PCT/DE95/00357

§ 371 Date: Nov. 20, 1996

§ 102(e) Date: Nov. 20, 1996

[87] PCT Pub. No.: WO95/25171

PCT Pub. Date: Sep. 21, 1995

[30] Foreign Application Priority Data

Mar. 17, 1994 [DE] Germany ............................. 44 09 663
Oct. 21, 1994 [DE] Germany ............................. 44 38 838

[51] Int. Cl.[7] ............................. C07H 21/04; C12N 9/50
[52] U.S. Cl. ......................... 435/219; 435/212; 435/226; 435/325; 435/410; 435/252.33; 435/320.1; 536/23.1; 536/23.2; 536/23.5
[58] Field of Search ..................................... 435/212, 219, 435/226, 252.3, 252.33, 325, 410, 320.1; 536/23.1, 23.2, 23.5

[56] References Cited

FOREIGN PATENT DOCUMENTS 0 685557   12/1995   European Pat. Off. .

OTHER PUBLICATIONS

Basset et al. "A novel metalloproteinase gene specifically expressed in stromal cells of breast carcinomas" Nature 348, 699–704, Dec. 1990.

Sato et al. "A matrix metalloproteinase expressed on the surface of invasive tumour cells" Nature 370, Jul. 1994.

Matrisian, et al. The Matrix–Degrading Metalloproteinase, *BioEssays*, 14:7, 455–463, 1992.

Will, et al. cDNA Sequence and mRNA tissue distribution of a novel human matrix metalloproteinase with a potential transmembrane segment, *Eur. J. Biochem.* 231:3, 602–608, 1995.

*Primary Examiner*—Rebecca E. Prouty
*Assistant Examiner*—Nashart T. Nashed
*Attorney, Agent, or Firm*—Foley & Lardner

[57] ABSTRACT

The invention relates to matrix metalloproteases and variants thereof and DNA sequences that encode these matrix metalloproteases. The invention further relates to obtaining the matrix metalloproteases from natural sources or by recombinant methods by expression of the DNA sequences. These matrix metalloproteases can also complexed with a ligand. The matrix metalloproteases are enzymes that hydrolyze one or more proteins of the extracellular matrix and are thought to contribute to local degradation of the extracellular matrix in tumor cell invasion and metastasis, rheumatoid arthritis, aneurysm formation, smooth muscle proliferation and migration processes in atherosclerotic disease.

15 Claims, 10 Drawing Sheets

FIG. 3A

```
                              10          20          30          40          50          60
                              .           .           .           .           .           .
MMPm1a.pep         MTYEMEHLFR------CLFA----ACVSSLV--FGSFFN--------HVVSFS---------
MMPm1b.pep         MS-PAPRPPR------CLL-------LPLLT--LGTALASLG---SAQSSSFS-PEAWLQQ
MMPm2.pep          MGSDPSAPGRPGWTGSLLGDREEAARPRLLPLLVLLGCLGLGVAAEDAEVH-AENWLRL
hscollr.pep        M--HSFPPL-------LLLLFWGVVS--------HSFPATLETQEQDV--DLVQKYLEK
hsclgna.pep        M--FSLKTL-------PFLLLLHVQIS-------KAFP--VSSKEKNT--KTVQDYLEK
p08253.swisspro    M--EALMARGALTGPLR-ALCLLGCLLSHAAAAPSPIIKFPGDVAPK-TDKELAVQYLNT
hs4cola.pep        M--------SLWQPLVLVLLVLGCCFAAPRQRQSTLVLFPGDLRTNLTDRQLAEEYLYR
hsmmp3a.pep        M--------KSL----PILLLLCVAVC---------SAYPLDGAARGEDTSMNLVQKYLEN
hsstrom2.pep       M--------MHL----AFLVLLCLPVC---------SAYPLSGAAKEEDSNKDLAQQYLEK
hsstrol3.pep       MA--------PAAWL---RSAAARALLPPMLLLLLQPPPLLARA----------------
                             *

MMPm1a.pep         FLFFESLALSSGVECNGAISAYCNLCLLGSSDSPASASQIAGKADADTMKAMRRPRCGVP
MMPm1b.pep         YGYLPPGDLRTHTQRSPQ------SLSAAIAAMQKFYGLQVTGKADADTMKAMRRPRCGVP
MMPm2.pep          YGYLPQPSRHMSTMRSAQI-----LASALAEMQRFYGIPVTGVLDEETKEWMKRPRCGVP
hscollr.pep        Y-YNLKNDGRQVEKRRNSGP----VVEKLKQMQEFFGLKVTGKPDAETLKVMKQPRCGVP
hsclgna.pep        F-YQLPSNQYQSTRKNGTNV----IVEKLKEMQRFFGLNVTGKPNEETLDMKKPRCGVP
p08253.swisspro    F-YGCPKE-------SCNLFV----LKDTLKKMQKFFGLPQTGDLDQNTIETMRKPRCGNP
hs4cola.pep        YGYTRVAEM------RGESKS---LGPALLLQKQLSLPETGELDSATLKAMRTPRCGVP
hsmmp3a.pep        Y-YDLEKDVKQFVRRKDSGP----VVKIREMQKFLGLEVTGKLDSDTLEVMRKPRCGVP
hsstrom2.pep       Y-YNLEKDVKQF-RRKDSNL----IVKKIQGMQKFLGLEVTGKLDTDTLEVMRKPRCGVP
hsstrol3.pep       ---LPPDVHHLHAERRGPQPWHAALPSSPAPAP------ATQEAPRPASSLRPPRCGVP
                                                                 +    ++    + +  ++  ****  *
```

FIG. 3B

```
MMPmla.pep      DKFGAEIKANV--RRKRYAIQGLKWQHNEITFCIQNYTPKVGEYATYEAIRKAFRVWESA
MMPmlb.pep      DKFGAEIKANV--RRKRYAIQGLKWQHNEITFCIQNYTPKVGEYATYEAIRKAFRVWESA
MMPm2.pep       DQFGVRVKANLRRRRKRYALTGRKWNNHHLTFSIQNYTEKLGWYHSMEAVRRAFRVWEQA
hscollr.pep     DVAQFVLTEGNP-------RWEQTHLTYRIENYTPDLPRADVDHAIEKAFQLWSNV
hsclgna.pep     DSGGFMLTPGNP-------KWERTNLTYRIRNYTPQLSEAEVERAIKDAFELWSVA
p08253.swisspro DVANYNFFPRKP-------KWDKNQITYRIIGYTPDLDPETVDDAFARAFQVWSDV
hs4cola.pep     DLGRFQTFEGDL-------KWHHHNITWIQNYSEDLPRAVIDDAFARAFALWSAV
hsmmp3a.pep     DVGHFRTFPGIP-------KWRKTHLTYRIVNTPDLPKDAVDSAVEKALKVWEEV
hsstrom2.pep    DVGHFSSFPGMP-------KWRKTHLTYRIVNTPDLPRDAVDSAIEKALKVWEEV
hsstrol3.pep    DPSDG---LSARNRQKRFVLSGGRWEKTDLTYRILRFPWQLVQEQVRQTMAEALKVWSDV
                *        *  *     *    *  *++*+    *     +   +* +    + +

MMPmla.pep      TPLRFREVPYAYIREGHEKQADIMIFFAEGFHGDSTPFDGEGGFLAHAYFPGPNIGGDTH
MMPmlb.pep      TPLRFREVPYAYIREGHEKQADIMIFFAEGFHGDSTPFDGEGGFLAHAYFPGPNIGGDTH
MMPm2.pep       TPLVFQEVPYEDIRLRRQKEADIMVLFASGFHGDSSPFDGTGGFLAHAYFPGPGLGGDTH
hscollr.pep     TPLTFTKV-------SEGQADIMISFVRGDHRDNSPFDGPGGNLAHAFQPGFQGIGGDAH
hsclgna.pep     SPLIFTRI-------SQGEADINIAFYQRDHGDNSPFDGPNGILAHAFQPGQGIGGDAH
p08253.swisspro TPLRFSRI-------HDGEADIMINFGRWEHGDGYPFDGKDGLLAHAFAPGTGVGGDSH
hs4cola.pep     TPLTFTRV-------YSRDADIVIQFGVAEHGDGYPFDGKDGLLAHAFPPGPGIQDAH
hsmmp3a.pep     TPLTFSRL-------YEGEADIMISFAVREHGDFYPFDGPGNVLAHAYAPGPGINGDAH
hsstrom2.pep    TPLTFSRL-------YEGEADIMISFAVKEHGDFYSFDGPGHSLAHAYPPGPGLYGDIH
hsstrol3.pep    TPLTFTEV-------HEGRADIMIDFARYWDGDDLPFDGPGGILAHAFFPKTHREGDVH
                +***    *        ** *     +   *     *  *****   +  **  +
```

FIG. 3C

```
MMPm1a.pep        FDSAEPWTVRNEDL-----------------
MMPm1b.pep        FDSAEPWTVRNEDL-----------------
MMPm2.pep         FDADEPWTFSSTDL-----------------
hscollr.pep       FDEHERWTNNFT-------------------
hsclgna.pep       FDAEETWTNTSA-------------------
p08253.swisspro   FDDDELWTLGEGQVVRVKYGNADGEYCKFPFLFNGKEYNSCTDTGRSDGFLWCSTTYNFE
hs4cola.pep       FDDDELWSLGKGVVVPTRFGNADGAACHFPFIFEGRSYSACTTDGRSDGLPWCSTTANYD
hsmmp3a.pep       FDDDEQWTKDTT-------------------
hsstrom2.pep      FDDDEKWTEDAS-------------------
hsstrol3.pep      FDYDETWTIGDDQ------------------
                  **  *   *  *+

MMPm1a.pep        ------------------------------
MMPm1b.pep        ------------------------------
MMPm2.pep         ------------------------------
hscollr.pep       ------------------------------
hsclgna.pep       ------------------------------
p08253.swisspro   KDGKYGFCPHEALFTMGGNAEGQPCKFPFRFQGTSYDSCTTEGRTDGYRWCGTTEDYDRD
hs4cola.pep       TDDRFGFCPSERLYTRDGNADGKPCQFPFIFQGQSYSACTTDGRSDGYRWCATTANYDRD
hsmmp3a.pep       ------------------------------
hsstrom2.pep      ------------------------------
hsstrol3.pep      ------------------------------
```

FIG. 3D

```
MMPm1a.pep      ------------------------------------------------------------
MMPm1b.pep      ------------------------------------------------------------
MMPm2.pep       ------------------------------------------------------------
hscollr.pep     ------------------------------------------------------------
hsclgna.pep     ------------------------------------------------------------
p08253.swisspro KKYGFCPETAMSTV-GGNSEGAPCVFPFTFLGNKYESCTSAGRSDGKMWCATTANYDDDR
hs4cola.pep     KLFGFCPTRADSTVMGGNSAGELCVFPFTFLGKEYSTCTSEGRGDGRLWCATTSNFDSDK
hsmmp3a.pep     ------------------------------------------------------------
hsstrom2.pep    ------------------------------------------------------------
hsstrol3.pep    ------------------------------------------------------------

MMPm1a.pep      ------NGNDIFLVAVHELGHALGLEHSSDPSAIMAPFYQ-WMDTENFVLPDDDRRGIQ
MMPm1b.pep      ------NGNDIFLVAVHELGHALGLEHSSDPSAIMAPFYQ-WMDTENFVLPDDDRRGIQ
MMPm2.pep       ------HGNNLFLVAVHELGHALGLEHSSNPNAIMAPFYQ-WKDVDNFKLPEDDLRGIQ
hscollr.pep     ------EYNLHRVAAHELGHSLGLSHSTDIGALMYPSY-TF--SGDVQLAQDDIDGIQ
hsclgna.pep     ------NYNLFLVAAHEFGHSLGLAHSSDPGALMYPNY-AFRETSNYSLPQDDIDGIQ
p08253.swisspro KWGFCPDQGYSLFLVAAHEFGHAMGLEHSQDPGALMAPIYT-YTK--NFRLSQDDIKGIQ
hs4cola.pep     KWGFCPDQGYSLFLVAAHEFGHALGLDHSSVPEALMYPMYR-FTE--GPPLHKDDVNGIR
hsmmp3a.pep     ------GTNLFLVAAHEIGHSLGLFHSANTEALMYPLYHSLTDLTRFRLSQDDINGIQ
hsstrom2.pep    ------GTNLFLVAAHELGHSLGLFHSANTEALMYPLYNSFTELAQFRLSQDDVNGIQ
hsstrol3.pep    ------GTDLLQVAAHEFGHVLGLQHTTAAKALMSAFYT-FRYP--LSLSPDDCRGVQ
                       +  +  ******+* **  **   *   **         *+*     * ++
```

FIG. 3E

```
MMPm1a.pep        QLYGGESG------------FPTKMPP--QP-RTTSRPSVPDKPKNPT-------------------
MMPm1b.pep        QLYGGESG------------FPTKMPP--QP-RTTSRPSVPDKPKNPT-------------------
MMPm2.pep         QLYGTPDG----QPQPTQPLPTVTPR--RPGRPDHRPPPQPPPGGKPERPKPGPPV
hscollr.pep       AIYGRSQN--------------------------------------PVQ--------PIGPQTPK
hsclgna.pep       AIYGLSSN--------------------------------------PIQ--------PTGPSTPK
p08253.swisspro   ELYGASPDIDL----------------------------GTGPT----------PTLGPVTP-----
hs4cola.pep       HLYGPREPEPRPPTTTPQPTAPPTVCPTGPPTVHPSERPTAGPTGPPSAGPTGPPTAG
hsmmp3a.pep       SLYGPPPD------------------------------------------SPETPLVPTEPVPPEPGTPA
hsstrom2.pep      SLYGPPPA-------------------------------------------STEEPLVPTKSVPSGSEMPA
hsstrol3.pep      HLYG----------QPWPTVTSR--TPALG-----------PQAGIDTNEIAP----L
                  +**                                               *

MMPm1a.pep        ------------YGPNICDGN--FDTVAMLRGEMFVFKERWFWRVRNNQVMD--GYPMPIGQF
MMPm1b.pep        ------------YGPNICDGN--FDTVAMLRGEMFVFKERWFWRVRNNQVMD--GYPMPIGQF
MMPm2.pep         QPRATERPDQYGPNICDGD--FDTVAMLRGEMFVFKGRWFWRVRHNRVLD--NYPMPIGHF
hscollr.pep       A-----------CDSKLTFDAITTIRGEVMFFKDRFYMR--TNPFYPEVELNF-TSVF
hsclgna.pep       P-----------CDPSLTFDAITTLRGEILFFKDRYFWR--RHPQLQRVEMNF--ISLF
p08253.swisspro   ------------EICKQDIVFDGIAQIRGEIFFFKDRFIWRTVTPRD--KPMGPLLVATF
hs4cola.pep       PSTATTVPLSPVDDACNVNI--FDAIAEIGNQLYLFKDGKYWRFSEGRGSRPQGPFLIADK
hsmmp3a.pep       N-----------CDPALSFDAVSTLRGEILIFKDRHFWR--KSLRKLEPELHL-ISSF
hsstrom2.pep      K-----------CDPALSFDAISTLRGEYLFFKDRYFWR--RSHWNPEPEFHL-ISAF
hsstrol3.pep      EPDAP-------PDACEAS--FDAVSTIRGELFFFKAGFVWRLRGGQLQP-GYPALASRH
                              *+   **++  ***+++ +  ***      +
```

FIG. 3F

```
MMPm1a.pep        WRGLPASINTAYER-KDGKFVFFKGDKHWVFDEASLEPGYPKHI-KELGRGLPTDKIDAA
MMPm1b.pep        WRGLPASINTAYER-KDGKFVFFKGDKHWVFDEASLEPGYPKHI-KELGRGLPTDKIDAA
MMPm2.pep         WRGLPGDISAAYER-QDGRFVFFKGDRYWLFREANLEPGYPQPL-TSYGLGIPYDRIDTA
hscollr.pep       WPQLPNGLEAAYEFADRDEVRFFKGNKYWAVQGQNVLHGYPKDIYSSFGFPRTVKHIDAA
hsclgna.pep       WPSLPTGIQAAYEDFDRDLIFLFKGNQYWALSGYDILQGYPKDI-SNYGFPSSVQAIDAA
p08253.swisspro   WPELPEKIDAVYEAPQEEKAVFFAGNEYWIYSASTLERGYPKPL-TSLGLPPDVQRVDAA
hs4cola.pep       WPALPRKLDSVFEEPLSKKLFFFSGRQVWVYTGASVL-G-PRRL-DKLGLGADVAQVTGA
hsmmp3a.pep       WPSLPSGVDAAYEVTSKDLVFIFKGNQFWAIRGNEVRAGYPRGIHT-LGFPPTVRKIDAA
hsstrom2.pep      WPSLPSYLDAAYEVNSRDTVFIFKGNEFWAIRGNEVQAGYPRGIHT-LGFPPTIRKIDAA
hsstrol3.pep      WQGLPSPVDAAFED-AQGHIWFFQGAQYWVYDGEKPVLG-PAPL-TELG--LVRFPVHAA
                  *  **      +   +  ++++*           *    +   *          +   *

MMPm1a.pep        LFWMPN-GKTYFFFRGNKYYRFNEELRAVDSEYPKNIK-VWEGIPESPRGSFMGSDEVFTY
MMPm1b.pep        LFWMPN-GKTYFFFRGNKYYRFNEELRAVDSEYPKNIK-VWEGIPESPRGSFMGSDEVFTY
MMPm2.pep         IWWEPT-GHTFFFQEDRYWRFNEETQRGDPGYPKPIS-VWQGIPASPKGAFLSNDAAYTY
hscollr.pep       LS-EENTGKTYFFVANKYWRYDEYKRSMDPGYPKMIAHDFPGIGHKVDAV--FMKDGFFY
hsclgna.pep       VF---YRSKTYFFVNDQFWRYDNQRQFMEPGYPKSISGAFPGIESKVDAV--FQQEHFFH
p08253.swisspro   FN-WSKNKKTYIFAGDKFWRYNEVKKKMDPGFPKLIADAWNAIPDNLDAVVDLQGGHSY
hs4cola.pep       LR-SGRGKM-LLFSGRRLWRFDVKAQMVDPRSASEVDRMFPGVP--LDTHDVFQYREKAY
hsmmp3a.pep       IS-DKEKNKTYFFVEDKYWRFDEKRNSMEPGFPKQIAEDFPGIDSKIDAV--FEEFGFFY
hsstrom2.pep      VS-DKEKKKTYFFAADKYWRFDENSQSMEQGFPRLIADDFPGVEPKVDAV--LQAFGFFY
hsstrol3.pep      LVWGPEKNKIYFFRGRDYWRFHPSTRRVDSPVPRRAT-DWRGVPSEIDAAFQDADG-YAY
                           *    *+   *+    +   +      +  +    +    +       +
```

FIG. 3G

```
MMPm1a.pep      FYKGNKYWKFNNQ-KLKVEPGYPKSALRDWMGC--------PSGGRP----DEGTEEET
MMPm1b.pep      FYKGNKYWKFNNQ-KLKVEPGYPKSALRDWMGC--------PSGGRP----DEGTEEET
MMPm2.pep       FYKGTKYWKFDNE-RLRMEPGYPKSILRDFMGCQEHVEPGPRWPDVARPPFNPHGGAEPGA
hscollr.pep     FFHGTRQYKFDPKT--KRILTL--QKANSWFNCRKNx-----------------------
hsclgna.pep     VFSGPRYYAFDLIA--QRVTRV--ARGNKWLNCRYGx-----------------------
p08253.swisspro FFKGAYYLKLENQS-LKSV-KFG-SIKSDWLGCx--------------------------
hs4cola.pep     FCQDRFYWRVSSRSELNQVDQVG-YVTYDILQCPEDx-----------------------
hsmmp3a.pep     FFTGSSQLEFDPNA--KKVTHT--LKSNSWLNCx--------------------------
hsstrom2.pep    FFSGSSQFEFDPNA--RMVTHI--LKSNSWLHCx--------------------------
hsstrol3.pep    FLRGRLYWKFDP-VKVKALEGFPRLVGPDFFGCAEPANTFLx------------------
                                   +                                *

MMPm1a.pep      EVIIEVDEEGGG------------------------------AVSAAAVVLPVLLLLVLAVGLAVF
MMPm1b.pep      EVIIEVDEEGGG------------------------------AVSAAAVVLPVLLLLVLAVGLAVF
MMPm2.pep       DSAEGDVGDGDGDFGAGVNKDGGSRVVVQMEEVARTVNVMVLVPLLLLLCVLGLTYALV
hscollr.pep     ------------------------------------------------------------
hsclgna.pep     ------------------------------------------------------------
p08253.swisspro ------------------------------------------------------------
hs4cola.pep     ------------------------------------------------------------
hsmmp3a.pep     ------------------------------------------------------------
hsstrom2.pep    ------------------------------------------------------------
hsstrol3.pep    ------------------------------------------------------------
```

FIG. 3H

```
MMPm1a.pep        FFRRHGTPRRLLYCQRSLLDKVx-------------------
MMPm1b.pep        FFRRHGTPRRLLYCQRSLLDKVx-------------------
MMPm2.pep         QMQRKGAPRVLLYCKRSLQEWVx-------------------
hscol1r.pep       ------------------------------------------
hsclgna.pep       ------------------------------------------
p08253.swisspro   ------------------------------------------
hs4cola.pep       ------------------------------------------
hsmmp3a.pep       ------------------------------------------
hsstrom2.pep      ------------------------------------------
hsstrol3.pep      ------------------------------------------
```

DNA SEQUENCES FOR MATRIX METALLOPROTEASES, THEIR PRODUCTION AND USE

BACKGROUND OF THE INVENTION

The invention relates to DNA sequences for human matrix metalloproteases as well as to homologous sequences derived therefrom. It furthermore relates to the proteins and protein variants, coded by the DNA sequences, their expression, preparation and utilization. Areas of application are molecular biological, medical and pharmaceutical research, medical diagnosis and therapy and the pharmaceutical and biotechnological industry.

Matrix metalloproteases hydrolyze proteins of the extracellular matrix. They change the matrix structure and effect cell-matrix interactions. The matrix metalloproteases include collagenases, gelatinases, stromelysins and metalloelastases [1]. The following are some of the physiological processes, in which the enzymes participate: ovulation [2], embryo implantation in the uterus [3], cell migrations and tissue inversions during embryo genesis [4], involution of the mammary gland [5] and of the uterus [6] and angiogenesis [7]. Matrix metalloproteases play an important role in wound healing and scar formation [8], in metastasizing of tumors cells [9, 10], in rheumatic arthritis and osteoarthritis [11, 12] and in periodontal diseases [13].

All matrix metalloproteases contain a $Zn^{2+}$ ion in the active center. The activation of the matrix metalloproteases, synthesized in the form of inactive proenzymes, requires the dissolution of a bond between the $Zn^{2+}$ ion in the active center and a Cys group in the N-terminal propeptide of matrix metalloproteases (cysteine switch) [14]. Matrix metalloproteases consist of several protein domains, which exhibit homology among members of the protease family [1, 14]. Whereas the protease matrilysin consists only of a propeptide and of the amino acid sequence of the catalytic domain, other matrix metalloproteases contain, in addition, a hemopexin-like sequence of about 200 amino acids. The gelatinases A and B contain additional amino acid sequences. Known human matrix metalloproteases, their molecular weights and their preferred substrates are listed in Table 1.

TABLE 1

MATRIX METALLOPROTEASES

| Protease | $M_r$ (kDa) | Substrate |
|---|---|---|
| Interstitial Collagenase (MMP-1) | 54.1 | Collagen I, II, III |
| Neutrophilic Collagenase (MMP-5) | 53.4 | Collagen I, II, III |
| Gelatinase A (MMP-2) | 73.9 | Collagen IV, V, VII Gelatin, Elastin |
| Gelatinase B (MMP-9) | 78.4 | Collagen IV, V Gelatin, Elastin |
| Stromelysin 1 (MMP-3) | 54 | Proteoglycans, Fibronectin, Laminin, Gelatin, Collagen II, IV, V, IX |
| Stromelysin 2 (MMP-10) | 54.1 | Proteoglycans, Fibronectin, Laminin, Gelatin, Collagen II, IV, V, IX |
| Matrilysin (MMP-7) | 29.7 | Proteoglycans, Fibronectin, Gelatin, Elastin |
| Stromelysin 3 | 54.6 | |
| Metalloelastase | 54 | Fibronectin, Elastin |

TABLE 1-continued

MATRIX METALLOPROTEASES

The different matrix metalloproteases are distinguished not only by a characteristic, macromolecular specificity for matrix proteins. Their activity is controlled on different molecular and cellular level:

1. Regulation of the synthesis of matrix metalloproteases by growth factors, cytokines, polypeptide hormones, prostaglandins, glucocorticoids, estrogen, progesterone and other effectors [1, 14].
2. Binding of matrix metalloproteases to membrane receptors [15].
3. Activation of inactive proenzymes by specific hydrolysis of the respective propeptides [16] or by oxidation [17].
4. Inhibition of matrix metalloproteases by specific protein inhibitors such as TIMP-I, TIMP-2 and TIMP-3 (TIMP=Tissue Inhibitor of Matrix Metalloproteases) [16].
5. Proteolytic degradation of matrix metalloproteases.

Matrix metalloproteases are being investigated intensively because of their important physiological functions and their role in the pathogenesis of diseases. There is interest in finding and characterizing further matrix metalloproteases.

SUMMARY OF THE INVENTION

It is an object of the present invention to make accessible novel and previously unknown human matrix metalloproteases for medical research, diagnosis and therapy. The task consists of identifying and isolating DNA sequences for matrix metalloproteases and of characterizing the proteins coded by the DNA sequences.

Novel matrix metalloproteases are discovered by the following method. In sequences of known matrix metalloproteases, conserved amino acid sequences are selected. Two suitable sequences are amino acids about a conserved Cys group in the propeptide (cysteine switch) and amino acids, which participate in the $Zn^{2+}$ binding in the active center of the enzymes. oligonucleotides are synthesized for the selected peptides. Polymerase chain reactions (PCR) are carried out with the oligonucleotides and cDNA, which can be obtained by reverse transcription of mRNA from cells and tissue. Synthesized DNA fragments are cloned and sequenced. The sequences determined are compared with sequences in gene data banks. PCR products with novel, previously unknown nucleotide sequences and homologous with DNA sequences of matrix metalloproteases are used as probes for determining the gene expression and for obtaining complete cDNA sequences from cDNA libraries. The nucleotide sequences of complete cDNA are determined. The amino acid sequences of the corresponding proteins are derived by translation of the coding nucleotide regions and analyzed by known methods.

BRIEF DESCRIPTION OF THE DRAWINGS

FIGS. 3A–3H show the homology comparison of MMPm1a (SEQ ID NO:1), MMPm1b (SEQ ID NO:2) and MMPm2 (SEQ ID NO:3) with known human matrix metalloproteases. The comparison was carried out with the CLUSTAL program. Key for the abbreviations in the figures: hscollr.pep (SEQ ID NO:16)—interstitial collagenase, hsclgna.pep (SEQ ID NO:17)—netrophile collagenases, PO8253.swisspro (SEQ ID NO:18)—gelatinase A, hs4cola.pep (SEQ ID NO:19)—gelatinase B, hsmmp3a.pep (SEQ ID NO:20)—stromelysin 1, hsstrom2.pep (SEQ ID NO:21)—stromelysin 2, hsstrol3.pep (SEQ ID NO:22)—stromelysin 3.

DETAILED DESCRIPTION OF THE INVENTION

Figure 1:
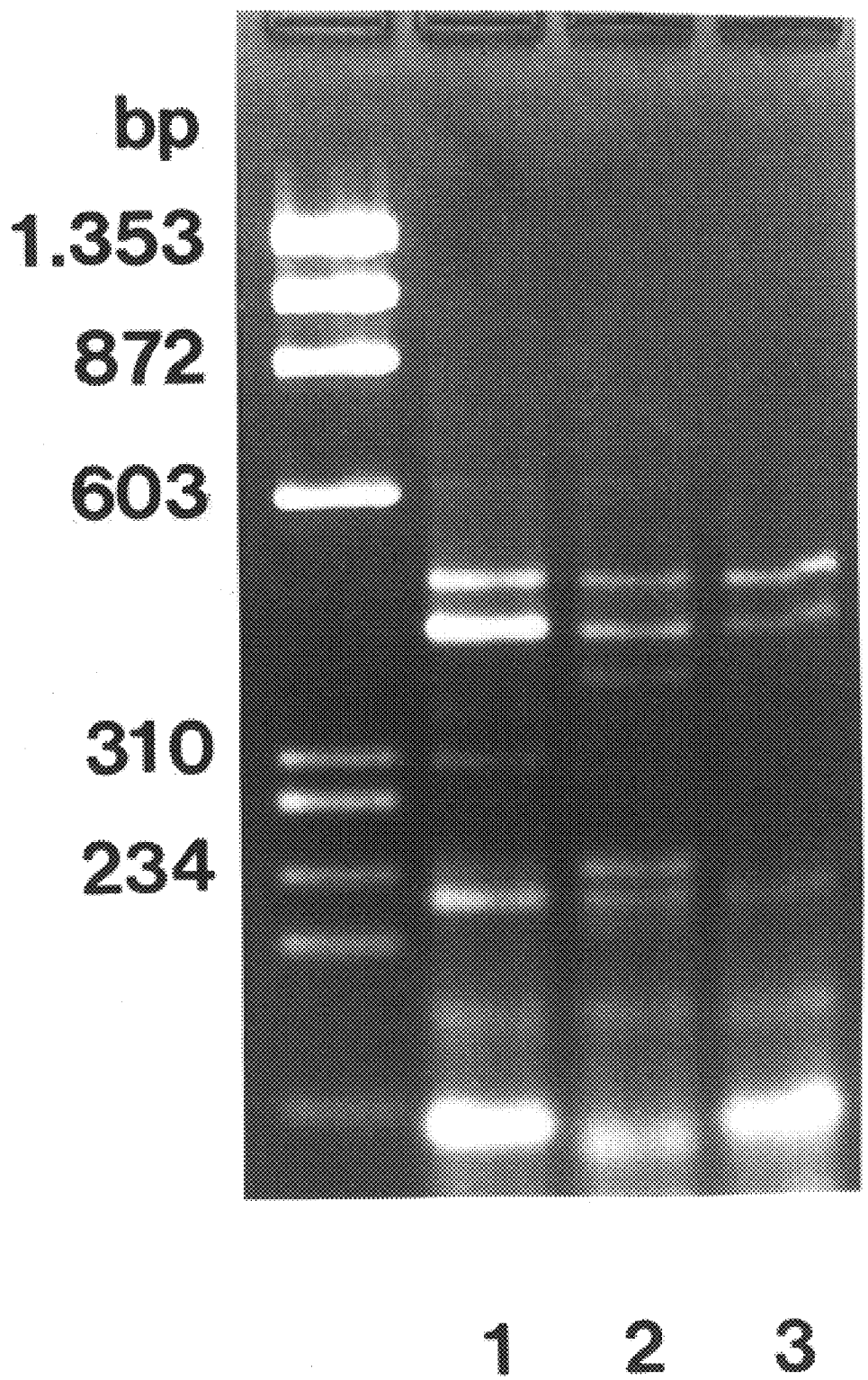
FIG. 1 shows an agarose gel electrophoresis of PCR products, which were obtained with degenerated primers for matrix metalloproteases and cDNA of the human neuroblastoma cell line SK-N-SH (lane 1), cDNA of kidney carcinoma tissue (lane 2) and cDNA of osteosarcoma tissue (lane 3).

The following cDNA sequences are found:
1. A cDNA sequence mmpm1a (SEQ ID NO:8) consisting of
   a 5' nontranslated region: base pairs 1 to 141
   a coding region: base pairs 142 to 1881
   a 3' nontranslated region: base pairs 1882 to 3456
2. A cDNA sequence mmpm1b (SEQ ID NO:9) consisting of
   a 5' nontranslated region: base pairs 1 to 113
   a coding region: base pairs 114 to 1862
   a 3' nontranslated region: base pairs 1863 to 3437
3. A cDNA sequence mmpm2 (SEQ ID NO:10) consisting of
   a 5' nontranslated region: base pairs 1 to 48
   a coding region: base pairs 49 to 2058
   a 3' nontranslated region: base pairs 2059 to 3530

The invention also comprises variants of these sequences as well as homologous DNA sequences of man and other mammalian species, which are found by cross-hybridization with these sequences. The invention also comprises constructs, which consist of a vector for the gene transfer in prokaryotic or eukaryotic cells and one of the inventive sequences.

Different aspects of the biosynthesis of coded matrix metalloproteases can be investigated with the help of the sequences mmpm1a, mmpm1b and mmpm2. The structure of the genes, including flanking sequences, can be determined. cDNA sequences can be used as molecular probes for analyzing the gene expression in cells and tissue.

The cDNA sequences mmpm1a (SEQ ID NO:8), mmpm1b (SEQ ID NO:9) and mmpm2 (SEQ ID NO:10) code encode the proteins with following amino acid sequences MMPm1a (SEQ ID NO:1), MMPm1b (SEQ ID NO:2) AND MMPm2 (SEQ ID NO:3), respectively.

The invention also comprises variants of these proteins, which are obtained by post-translational protein modifications, by chemical modifications of the proteins or by in vitro mutagenesis and expression of nucleotide sequences, as well as of homologous proteins of man and other mammalian species, which are identified by immunological cross-reactivity or comparable enzyme activity. The invention also comprises complexes of these proteins with one or several ligands.

MMPm1a (SEQ ID NO:1), MMPm1b (SEQ ID NO:2) and MMPm2 (SEQ ID NO:3) can also be isolated from natural sources. The proteins can also be synthesized by gene transfer and expression in prokaryotic and eukaryotic cells and obtained from the recombinant cells. The availability of the proteins MMPm1a, MMPm1b and MMPm2 enables their structure and function to be investigated. Methods for determining enzymatic activity and specificity can be worked out. Beginning with the primary structure of the proteins MMPm1a, MMPm1b and MMPm2, monoclonal and polycolonal antibodies can be produced. The antibodies can be used for the diagnostic analysis of MMPm1a, MMPm1b and MMPm2. MMPm1a, MMPm1b and MMPm2 can be used as test structures for finding natural and synthetic activators and inhibitors of matrix metalloproteases.

The following additional statements can be made concerning the characterization of mmpm1a, mmpm1b and mmpm2 and of MMPm1a, MMPm1b and MMPm2. The DNA sequences mmpm1a and mmpm1b differ only in their 5' nontranslated regions and in the immediately subsequent parts of their coding regions. starting with the nucleotides 363 (mmpm1a) and 344 (mmpm1b) respectively, the two sequences are identical. The mmpm1a sequence contains an open reading frame of 580 codons. The reading frame commences with the nucleotides $A_{142}TG$. However, the surroundings of these nucleotides are unfavorable for a effective translation. On the other hand, the subsequent nucleotides $A_{154}TG$ in the reading frame are in an environment favoring a translation start. It is possible that the translation of mmpm1a commences only at the $A_{154}TG$. Starting with $A_{114}TG$, the mmp1b sequence has an open reading frame of 583 codons. The starting codon is within the nucleotide sequence ACCATGT, which favors an effective translation. The translation start of mmpm2 is found at $A_{49}TG$. The open reading frame of mmpm2 contains 670 codons.

The proteins MMPm1a, MMPm1b and MMPm2, which are encoded by the cDNA sequences mmpm1a, mmpm1b and mmpm2, have calculated molecular weights of 65,591, 65,900 and 75,813. The primary sequences of MMPm1a, MMPm1b and MMPm2 are homologous with sequences of known matrix metalloprotleases. Each of the three novel enzymes contains a signal peptide, a prosequence with the cysteine switch region PRCGVPD (SEQ ID NO:11) and a consensus sequence RRKRYA (SEQ ID NO:12). Catalytic domains with the specific arrangement of three histidine groups HELGHALGLEH (SEQ ID NO:13) and sequences homologous with hemopexin follow. In contrast to known matrix metalloproteases, MMPm1a, MMPm1b and MMPm2 furthermore contain C-terminal sequences with characteristic sequences of hydrophobic amino acid groups. MMPm1a and MMPm1b have the hydrophobic amino acid sequence AAAVVLPVLLLLLVLAVGLAV (amino acid positions 536–556 in MMPm1a, amino acid positions 539–559 in MMPm1b). An analogous sequence in MMPm2 is VVMVLVPLLLLLCVLGLTY (amino acid groups 626–645). The hydrophobic sequences, which go beyond the positions given, are flanked by charged amino acid groups. N-terminally, negatively charged glutamine and aspartate groups predominate and C-terminally, positively charged arginine and lysine groups predominate.

The presence of the hydrophobic sequences in MMPm1a, MMPm1b and MMPm2 permits the conclusion to be drawn that MMPm1a, MMPm1b and MMPm2, contrary to known soluble matrix metalloproteases (Table 1), are membrane-associated enzymes. It follows from the primary sequences that propeptides, catalytic domains and domains of the proteases, homologous with hemopexin, are localized extracellularly. The outermost C termini of the proteins, on the other hand, should be located in the cytosol of cells expressing MMPm1a, MMPm1b and MMPm2.

MMPm1a, MMPm1b and MMPm2 contain a potential glycosylating site.

MMPm1a and MMPm1b differ only in their signal and prosequences. The different structure of the prosequences implies different activation mechanisms of MMPm1a and MMPm1b. Since the prosequences are cleaved off by hydrolysis in the course of the activation of matrix metalloproteases, the activation of MMPm1a and MMPm1b should lead to an identical, active enzyme.

Figure 2A:
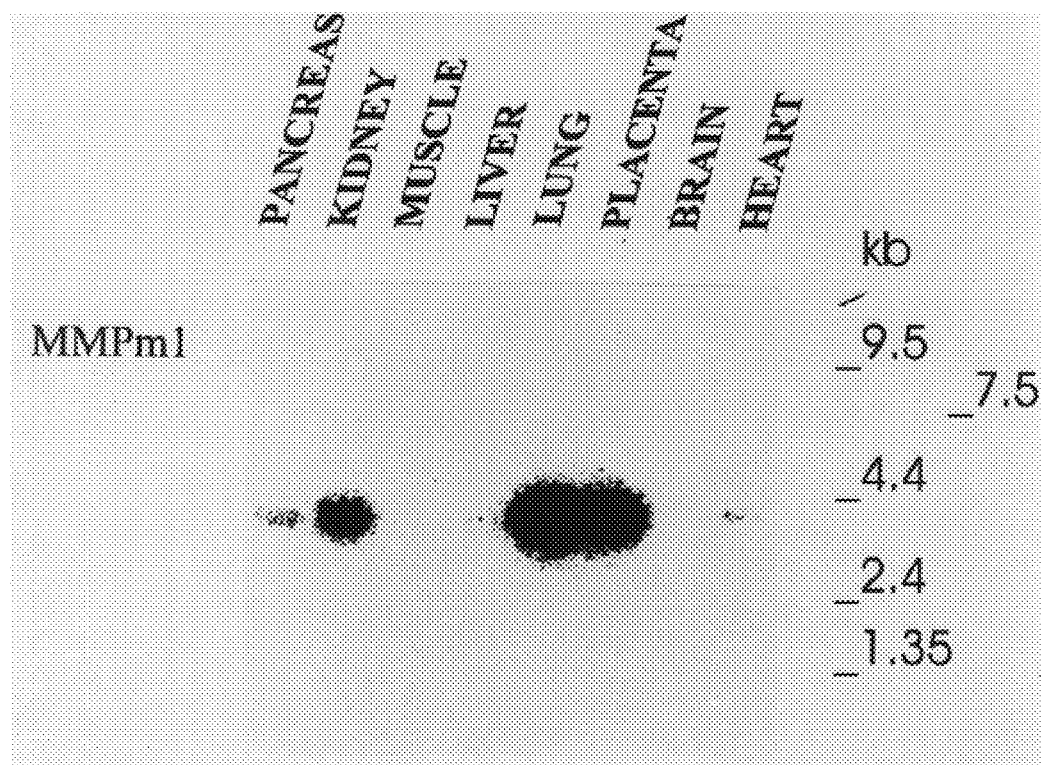
FIGS. 2A and 2B show the Northern Blot Analysis of mRNA for MMPm1 (FIG. 2A) and MMPm2 (FIG. 2B) in different human tissue.
Figure 2B:
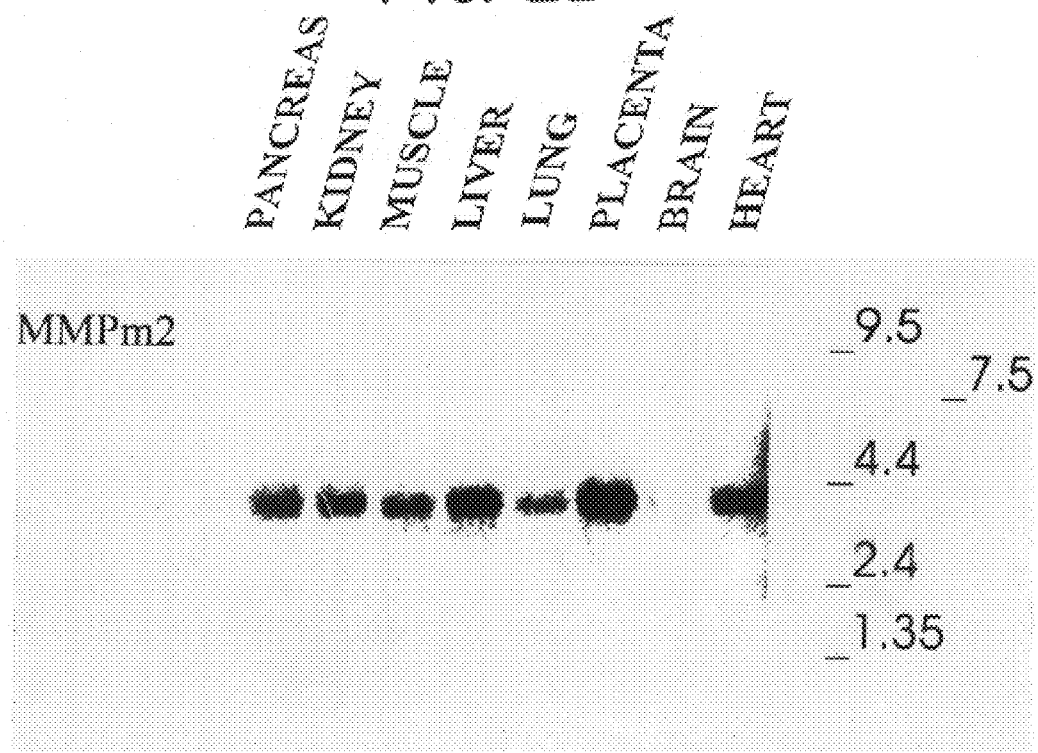

As shown in FIGS. 2A and 2B, Northern blot analyses of mRNA of human tissue confirm that MMPm1 and MMPm2 are expressed differently. Matrix metalloproteases of the MMPm1 type are expressed primarily in lung, placenta, kidney, ovary, prostate, small intestine, spleen, thymus and testicle tissue. Their expression is clearly less in heart and pancreas tissue and hardly detectable in the brain, liver and skeletal muscles. MMPm2 is expressed in the placenta, heart, liver, skeletal muscles, kidneys, pancreas, lung, testicle, colon and small intestine.

In summary, it is noted that the invention makes available novel, previously not known matrix metalloproteases of man. A knowledge of the cDNA and protein sequences of the matrix metalloproteases permits the biosynthesis, structure and function of the enzymes to be investigated further. Inherited and acquired mutations can be found by analyzing gene sequences. Diagnostic information can be obtained from determining the concentration and activity of matrix metalloproteases in cells, tissues and excreta. The enzymes can be used advantageously as test structures for discovering new pharmaceutical drugs, including activators and inhibitors of matrix metalloproteases.

The invention is described further by the following examples:

1. Identification of Novel DNA Sequences for Matrix Metalloproteases

For finding cDNA sequences, which code for matrix metalloproteases, mRNA was isolated from human cell and tumor tissue, including neuroblastoma cells, kidney carcinoma and osteosarcoma tissue. The mRNA was transcribed into cDNA with reverse transcriptase.

Two preserved amino acid sequences were selected from the protein sequences of known matrix metalloproteases.

1. A sequence about a characteristic Cys group in propeptides in matrix metalloproteases

P-R-C-G-V/N-P-D (SEQ ID NO:4)

2. A sequence with three HIS groups in the catalytic protein domain of matrix metalloproteases ($Zn^{2+}$ binding region):

H-E-L/I/F-G-H-S/V/A-L/M-G (SEQ ID NO:5)

Corresponding to the amino acid sequences, degenerate oligo-nucleotide primers, which take into consideration the variation of the amino acids in the two conseserved sequences, as well as the degeneracy of the genetic code, were synthesized:

1. Propeptide primer (Seq. ID no.: 6)

```
5'- NN TCT AGA CCC AGI TGT GGI GTI CCI GA - 3'
              C          AA
```

2. Zn binding region primer (Seq. ID no.: 7)

```
5' - NN GGA TCC CC CAT IGA ATG ICC IAI TTC ATG - 3'
             G CC  G            C   G
```

Both primers contain four desoxyinosine nucleotides as well as additional nucleotides for identification sites of the restriction endonucleases XbaI (propeptide primer) and BamHI ($Zn^{2+}$ binding region primer).

The degenerated primers were used together with cDNA in the PCR.

The reaction mixture contained:

100 ng cDNA
1 μg propeptide primer
1 μg $Zn^2$ bonding region primer
2.5 μ/100 μL DNA polymerase AmpliTaq
100 μM dNTP
0.01% gelatin
50 mM KCl
1.5 mM $MgCl_2$
10 mM Tris HCl, pH 8.3

In all, 30 reaction cycles of the sequence, 50 seconds at 94° C., 1 minute at 56° C. and 2 minutes at 72° C., were carried out. The amplified DNA was extracted with phenol/chloroform and subsequently treated with the restriction enzymes XbaI and BamHI. DNA fragments, ranging in size from 350 to 500 base pairs, were isolated by Agarose gel electrophoresis (FIG. 1) and cloned in the plasmid pBluescript SK (Stratagene). Individual clones were sequenced with T3 and T7 primers and sequenase 2.0 (USB/Amersham Life Science). The sequences obtained were compared with DNA sequences in the Genbank and EMBL data banks. The sequences were compared with the FASTA program of the HUSAR (GCG Package, Copyright Genetics Computer Group, Inc.) program package. Beginning with the kidney carcinoma cDNA, for example, several hundred clones with amplified DNA were obtained, of which 50 were sequenced. The evaluation revealed known as well as novel DNA sequences. The former included sequences for human interstitial collagenase and for matrilysin. The latter included two sequences homologous to human matrix metalloproteases. The two novel sequences, which were named PCRmmpm1 and PCRmmpm2, contain the nucleotides of SEQ ID NO:14 and SEQ ID NO:15, respectively.

PCRmmpm2 (SEQ ID NO:15)

```
TCTAGACCCAGGTGCGGGAAGCCGGACCAGTTCGGGGTACGAGTGAAAGCCAACCTGCGGCGGCGTCGGA

AGCGCTACGCCCTCACCGGGAGGAAGTGGAATAACCAACCATCTGACCTTTAGCATCCAGAACTACACCG

GAGAAGTTGGGCTGGTACCACTCGATGGAGGCGGTGCGCAGGGCCTTCCGCGTGTGGGAGCAGGCCACGC

CCCTGGTCTTCCAGGAGGTGCCCTATGAGACATCCGGCTGCGGCGACAGAAGGAGGCCGACATCATGGTA

CTCTTTCCCTCTGGCTTCCACGGCGAACAGCTCGCCGTTTGATGGCACCGGTGGCTTTCTGGCCCACGCC

TATTTCCCTGGCCCCGGCCTAGGCGGGGACACCCATTTTGACGCAGATGAGCCCTGGACCTTCTCCAGCA

CTGACCTGCATGGAAACAACCTCTTCCTGGTGGCAGTGCATGAGCTGGGCCACGCGCTGGGGGATCC
```

2. Northern Blot Analysis

The expression of matrix metalloproteases in human tissue was investigated with the help of the PCRmmpm1 and PCRmmpm2 fragments. The fragments were labeled radioactively (Multiprime DNA-Labeling Kit, Amersham Life Science) and hybridized with mRNA on nylon (Multiple Tissue Blot, Clontech). The hybridizations and subsequent washings took place under standard conditions [18].

PCRmmpm1 and PCRmmpm2 hybridized with RNA of about 3.6 kb. However, experiments confirm a different expression of the mRNA hybridizing with PCRmmpm1 and PCRmmpm2 (FIGS. 2A and 2B). Specific transcripts, which hybridize with PCRmmpm1, are contained particularly in lung, placenta, kidney and kidney carcinoma tissue (not shown). They are represented in clearly lesser amounts in pancreas and heart tissue and hardly at all in the liver, skeletal muscle and brain.

Messenger RNA, which hybridizes with PCRmmpm2, is synthesized particularly in placenta tissue. Its expression, however, is comparable in the heart, liver, skeletal muscle, kidneys, pancreas and lung and clearly less in brain tissue.

3. Isolation and Sequencing of cDNA mmpm1 and mmpm2

A lung cDNA bank in the λgt 11 vector (Clontech) was analyzed by means of phage transfer on nylon and hybridization with the radioactively labeled PCRmmpm1 and PCRmmpm2 probes [18]. The hybridizations were carried out for 16 hours at 40° C. in 50% formamide, 5×SSPE, 5×Denhardt, 0.5% SDS and 50 μg/mL denatured herring sperm DNA. After the hybridization, the filters were washed at room temperature and at 65° C. in 2×SSC, 0.1% SDS and subsequently evaluated in a Bio-Imaging-Analyzer (BAS 2000, Fuji Photo Film Co., LTD). Phage clones, which hybridized with PCRmmpm1 and PCRmmpm2, were identified by means of specifically bound radioactivity. The phages found were isolated stepwise by dilution. The DNA of isolated phages was isolated (Quiagen Lambda Kit, Diagen GmbH) and the cDNA inserts contained were inserted into the plasmid vector pBluescript SK (Stratagene). The inserts subsequently were divided into partial fragments (Erase-a-Base-System, Promega) and sequenced (Sequenase 2.0, USB/Amersham Life Science). DNA sequences detected were analyzed with the help of the DNA-STAR (DAN-STAR. Inc) and HUSAR (GCT Package, Copyright Genetics Computer Group, Inc) program packages. The translation of the coding sequences and the comparison of the amino acid sequences obtained with known matrix metalloproteases confirmed that the novel sequences belong to the family of matrix metalloproteases (FIGS. 3A–3D).

REFERENCES

1. Matrisian, L. M. (1992) Bioassays 14, 455–463
2. Curry, T. E. jr, Mann, J. S., Estes, R. J. and Jones, P. B. C. (1990) Endocrinology 127, 63–68
3. Librach, C. L., Werb, Z., Fitzgerald, M. L., Chiu, K., Corwin, N. M., Esteves, R. A., Grobelny, D., Galardy, R., Damsky, C. H. and Fisher, S. J. (1991) J. Cell Biol. 113, 437–449
4. Brenner, C. A., Adler, R. R., Rappolee, D. A., Pedersen, R. A. and Werb, Z. (1989) Genes Development 3, 848–859
5. Talhouk, R. S., Bissel, M. J. and Werb, Z. (1992) J. Cell Biol. 118, 1271–1282
6. Woessner, J. F and Taplin, C. (1988) J. Biol. Chem. 263, 16918–16925
7. Folkman, J. and Shing, Y. (1992) J. Biol. Chem. 267, 10931–10934
8. Sakamoto, S. and Sakamoto, M. (1988) Mol. Aspects Med. 10, 301–428
9. Mignatti, P. and Rifkin, D. B. (1993) Physiol. Rev. 73, 161–195
10. Stetler-Stevenson, W. G., Liotta, L. A. and Kleiner, D. E. jr (1993), FASEB J. 7, 1434–1441
11. Dean, D. D., Martel-Pelletier, J., Pelletier, J.-P., Howell, D. S. and Woessner, J. F. jr, (1989) J. Clin. Invest. 84, 678–685
12. McCachren, S. S. (1991) Arthritis Rheum. 34, 1085–1093
13. Birkedahl-Hansen, H. (1993) J. Periodontol. 64, 474–484
14. Woessner, J. F. jr (1991) FASEB J. 5, 2145–2154
15. Monsky, W. L., Kelly, T., Lin, C.-Y., Yeh, Y., Stetler-Stevenson, W. G., Mueller, S. C. and Chen, W.-T. (1993) Cancer Res. 53, 3159–3164
16. Kleiner, D. E. jr and Stetler-Stevenson, W. G. (1993) Curr. Opinion Cell Biol. 5, 891–897
17. Weiss, S. J., Peppin, G., Ortiz, X., Ragsdale, C. and Test, S. T. (1985) Science 227, 747–749
18. Sambrook, J., Fritsch, D. F. and Maniatis, T. (1989) Molecular Cloning. A Laboratory Manual. 2nd Edition. Cold Spring Harbor Laboratory Press.

---

What is claimed is:

1. An isolated DNA sequence encoding a matrix metalloprotease, wherein said DNA sequence comprises:
   a) a DNA sequence encoding SEQ ID NO:1;
   b) a DNA sequence encoding SEQ ID NO:2;
   c) a DNA sequence encoding SEQ ID NO:3;
   d) SEQ ID NO:8;
   e) SEQ ID NO:9;
   f) SEQ ID NO:10; or
   g) a DNA sequence that hybridizes to any one of d), e) or f) at 40° C. in a solution of 50% formamide in 5×SSPE/5×Denhardt solution containing 0.5% SDS and 50 μg/ml denatured carrier DNA.

2. The isolated DNA sequence of claim 1, wherein said DNA sequence is SEQ ID NO:8.

3. The isolated DNA sequence of claim 1, wherein said DNA sequence is SEQ ID NO:9.

4. The isolated DNA sequence of claim 1, wherein said DNA sequence is SEQ ID NO:10.

5. A prokaryotic or eukaryotic vector comprising a DNA sequence of claim 1 encoding a matrix metalloprotease.

6. The vector of claim 5 comprising the DNA sequence of SEQ ID NO:9.

7. The vector of claim 5 comprising the DNA sequence of SEQ ID NO:10.

8. A prokaryotic or eukaryotic cell transformed with the vector of claim 5, wherein said cell expresses a matrix metalloprotease encoded by said DNA sequence.

9. The cell of claim 8, wherein said DNA sequence is SEQ ID NO:9.

10. The cell of claim 8 comprising the DNA sequence is SEQ ID NO:10.

11. A purified matrix metalloprotease comprising:
   a) SEQ ID NO:1;
   b) SEQ ID NO:2;

c) SEQ ID NO:3; or d) a variant of a), b) or c) obtained by post-translational protein modification, chemical modification, or by expression of an in vilto mutagenized DNA sequence in recombinant cells containing a DNA sequence selected from the group consisting of:
   i) a DNA sequence encoding SEQ ID NO:1;
   ii) a DNA sequence encoding SEQ ID NO:2;
   iii) a DNA sequence encoding SEQ ID NO:3;
   iv) SEQ ID NO:8;
   v) SEQ ID NO:9;
   vi) SEQ ID NO:10; and
   vii) a DNA sequence that hybridizes to any one or iv), v) or vii) at 40° C. in a solution of 50% formamide in 5×SSPE/5×Denhardt solution containing 0.5% SDS and 50 µg/ml denatured carrier DNA, wherein said variant possesses immunological cross-reactivity or comparable matrix metalloprotease activity to said matrix metalioproteases of a), b) or c).

12. The purified matrix metalloprotease of claim 11 comprising SEQ ID NO:1.

13. The purified matrix metalloprotease of claim 11 comprising SEQ ID NO:2.

14. The purified matrix metalloprotease of claim 11 comprising SEQ ID NO:3.

15. A method of producing a matrix metalloprotease of claim 11 comprising:

i) obtaining said matrix metalloprotease from natural sources, or ii) obtaining said matrix metalloprotease from recombinant cells expressing a DNA sequence encoding a matrix metalloprotease selected from the group consisting of:
   a) a DNA sequence encoding SEQ ID NO:1;
   b) a DNA sequence encoding SEQ ID NO:2;
   c) a DNA sequence encoding SEQ ID NO:3;
   d) SEQ ID NO:8;
   e) SEQ ID NO:9;
   f) SEQ ID NO:10; or
   g) a DNA sequence that hybridizes to any one of d), e) or f) at 40° C. in a solution of 50% formamide in 5×SSFE/5×Denhardt solution containing 0.5% SDS and 50 µg/ml denatured carrier DNA.

* * * * *

UNITED STATES PATENT AND TRADEMARK OFFICE
CERTIFICATE OF CORRECTION

PATENT NO.   : 6,114,159
DATED        : September 5, 2000
INVENTOR(S)  : Will Horst and Bernd Hinzmann It is certified that error appears in the above-identified patent and that said Letters Patent is hereby corrected as shown below:

Column 3,
Line 53, delete "code"
Line 53, after the words "proteins with" insert -- the --;
Line 55, delete "AND" replace it with -- and --.

Column 6,
Line 52, delete the line beginning with "PCRmmpm2" through the next seven lines of genetic code ending at "GGGGGATCC".

Column 51,
Line 50, please amend claim 1 as follows:
    1.    An isolated DNA sequence encoding a matrix mettaloprotease, wherein said DNA sequence comprises:
    a)    a DNA sequence encoding SEQ ID NO:1;
    b)    a DNA sequence encoding SEQ ID NO:2;
    c)    a DNA sequence encoding SEQ ID NO:3;
    d)    SEQ ID NO: 8;
    e)    SEQ ID NO: 9; or
    f)    SEQ ID NO: 10.

Column 52,
Line 65, please amend claim 11 as follows:
    11.    A purified matrix mettaoprotease comprising:
    a)    SEQ ID NO. 1;
    b)    SEQ ID NO. 2;
    c)    SEQ ID NO. 3; or
    d)    a matrix metalloprotease obtained by expression of a DNA sequence in recombinant cells, wherein said DNA sequence is selected from the group consisting of:
    i)    a DNA sequence encoding SEQ ID NO:1;
    ii)    a DNA sequence encoding SEQ ID NO:2;
    iii)    a DNA sequence encoding SEQ ID NO:3;
    iv)    SEQ ID NO: 8;
    v)    SEQ ID NO:9; and
    vi)    SEQ ID NO; 10.

UNITED STATES PATENT AND TRADEMARK OFFICE
CERTIFICATE OF CORRECTION

PATENT NO.   : 6,114,159
DATED        : September 5, 2000
INVENTOR(S)  : Will Horst and Bernd Hinzmann It is certified that error appears in the above-identified patent and that said Letters Patent is hereby corrected as shown below:

Column 54,
Line 3, please amend claim 15 as follows:
    15.    A method of producing a matrix mettalloprotease of claim 11 comprising:
    i)    obtaining said matrix metalloprotease from natural sources, or
    ii)    obtaining said matrix metalloprotease from recombinant cells expressing a DNA sequence encoding a matrix metallopretease wherein said DNA selected from the group consisting of:
    a)    a DNA sequence encoding SEQ ID NO: 1;
    b)    a DNA sequence encoding SEQ ID NO: 2;
    c)    a DNA sequence encoding SEQ ID NO: 3;
    d)    SEQ ID NO: 8;
    e)    SEQ ID NO: 9; and
    f)    SEQ ID NO: 10.

Signed and Sealed this

Thirtieth Day of July, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 579 amino acids
      (B) TYPE: amino acid
      (C) STRANDEDNESS: single
      (D) TOPOLOGY: linear (xi) SEQUENCE DESCRIPTION: SEQ ID NO:1:

```
Met Thr Tyr Glu Met Glu His Leu Phe Arg Cys Leu Phe Ala Ala Cys
 1               5                  10                  15

Val Ser Ser Leu Val Phe Gly Ser Phe Phe Asn His Val Val Ser Phe
```

-continued

```
                20                  25                  30
Ser Phe Leu Phe Phe Glu Ser Leu Ala Leu Ser Ser Gly Val Glu Cys
        35                  40                  45

Asn Gly Ala Ile Ser Ala Tyr Cys Asn Leu Cys Leu Leu Gly Ser Ser
 50                  55                  60

Asp Ser Pro Ala Ser Ala Ser Gln Ile Ala Gly Lys Ala Asp Ala Asp
 65                  70                  75                  80

Thr Met Lys Ala Met Arg Arg Pro Arg Cys Gly Val Pro Asp Lys Phe
                 85                  90                  95

Gly Ala Glu Ile Lys Ala Asn Val Arg Arg Lys Arg Tyr Ala Ile Gln
                100                 105                 110

Gly Leu Lys Trp Gln His Asn Glu Ile Thr Phe Cys Ile Gln Asn Tyr
                115                 120                 125

Thr Pro Lys Val Gly Glu Tyr Ala Thr Tyr Glu Ala Ile Arg Lys Ala
                130                 135                 140

Phe Arg Val Trp Glu Ser Ala Thr Pro Leu Arg Phe Arg Glu Val Pro
145                 150                 155                 160

Tyr Ala Tyr Ile Arg Glu Gly His Glu Lys Gln Ala Asp Ile Met Ile
                165                 170                 175

Phe Phe Ala Glu Gly Phe His Gly Asp Ser Thr Pro Phe Asp Gly Glu
                180                 185                 190

Gly Gly Phe Leu Ala His Ala Tyr Phe Pro Gly Pro Asn Ile Gly Gly
                195                 200                 205

Asp Thr His Phe Asp Ser Ala Glu Pro Trp Thr Val Arg Asn Glu Asp
                210                 215                 220

Leu Asn Gly Asn Asp Ile Phe Leu Val Ala Val His Glu Leu Gly His
225                 230                 235                 240

Ala Leu Gly Leu Glu His Ser Ser Asp Pro Ser Ala Ile Met Ala Pro
                245                 250                 255

Phe Tyr Gln Trp Met Asp Thr Glu Asn Phe Val Leu Pro Asp Asp Asp
                260                 265                 270

Arg Arg Gly Ile Gln Gln Leu Tyr Gly Gly Glu Ser Gly Phe Pro Thr
                275                 280                 285

Lys Met Pro Pro Gln Pro Arg Thr Thr Ser Arg Pro Ser Val Pro Asp
290                 295                 300

Lys Pro Lys Asn Pro Thr Tyr Gly Pro Asn Ile Cys Asp Gly Asn Phe
305                 310                 315                 320

Asp Thr Val Ala Met Leu Arg Gly Glu Met Phe Val Phe Lys Glu Arg
                325                 330                 335

Trp Phe Trp Arg Val Arg Asn Asn Gln Val Met Asp Gly Tyr Pro Met
                340                 345                 350

Pro Ile Gly Gln Phe Trp Arg Gly Leu Pro Ala Ser Ile Asn Thr Ala
                355                 360                 365

Tyr Glu Arg Lys Asp Gly Lys Phe Val Phe Lys Gly Asp Lys His
                370                 375                 380

Trp Val Phe Asp Glu Ala Ser Leu Glu Pro Gly Tyr Pro Lys His Ile
385                 390                 395                 400

Lys Glu Leu Gly Arg Gly Leu Pro Thr Asp Lys Ile Asp Ala Ala Leu
                405                 410                 415

Phe Trp Met Pro Asn Gly Lys Thr Tyr Phe Phe Arg Gly Asn Lys Tyr
                420                 425                 430

Tyr Arg Phe Asn Glu Glu Leu Arg Ala Val Asp Ser Glu Tyr Pro Lys
435                 440                 445
```

```
Asn Ile Lys Val Trp Glu Gly Ile Pro Glu Ser Pro Arg Gly Ser Phe
    450                 455                 460

Met Gly Ser Asp Glu Val Phe Thr Tyr Phe Tyr Lys Gly Asn Lys Tyr
465                 470                 475                 480

Trp Lys Phe Asn Asn Gln Lys Leu Lys Val Glu Pro Gly Tyr Pro Lys
                485                 490                 495

Ser Ala Leu Arg Asp Trp Met Gly Cys Pro Ser Gly Gly Arg Pro Asp
                500                 505                 510

Glu Gly Thr Glu Glu Thr Glu Val Ile Ile Glu Val Asp Glu
                515                 520                 525

Glu Gly Gly Gly Ala Val Ser Ala Ala Val Val Leu Pro Val Leu
530                 535                 540

Leu Leu Leu Val Leu Ala Val Gly Leu Ala Val Phe Phe Phe Arg
545                 550                 555                 560

Arg His Gly Thr Pro Arg Arg Leu Leu Tyr Cys Gln Arg Ser Leu Leu
                565                 570                 575

Asp Lys Val (2) INFORMATION FOR SEQ ID NO:2:

(i) SEQUENCE CHARACTERISTICS:
        (A) LENGTH: 582 amino acids
        (B) TYPE: amino acid
        (C) STRANDEDNESS: single
        (D) TOPOLOGY: linear (xi) SEQUENCE DESCRIPTION: SEQ ID NO:2:

Met Ser Pro Ala Pro Arg Pro Arg Cys Leu Leu Pro Leu Leu
1               5                   10                  15

Thr Leu Gly Thr Ala Leu Ala Ser Leu Gly Ser Ala Gln Ser Ser Ser
                20                  25                  30

Phe Ser Pro Glu Ala Trp Leu Gln Gln Tyr Gly Tyr Leu Pro Pro Gly
                35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
                100                 105                 110

Ala Ile Gln Gly Leu Lys Trp Gln His Asn Glu Ile Thr Phe Cys Ile
                115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
                180                 185                 190

Asp Gly Glu Gly Gly Phe Leu Ala His Ala Tyr Phe Pro Gly Pro Asn
                195                 200                 205

Ile Gly Gly Asp Thr His Phe Asp Ser Ala Glu Pro Trp Thr Val Arg
    210                 215                 220
```

```
Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
            245                 250                 255

Met Ala Pro Phe Tyr Gln Trp Met Asp Thr Glu Asn Phe Val Leu Pro
        260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Glu Thr Glu Val Ile Ile Ile Glu
        515                 520                 525

Val Asp Glu Glu Gly Gly Ala Val Ser Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580
```

(2) INFORMATION FOR SEQ ID NO:3:

(i) SEQUENCE CHARACTERISTICS:
        (A) LENGTH: 669 amino acids
        (B) TYPE: amino acid
        (C) STRANDEDNESS: single
        (D) TOPOLOGY: linear -continued (xi) SEQUENCE DESCRIPTION: SEQ ID NO:3:

```
Met Gly Ser Asp Pro Ser Ala Pro Gly Arg Pro Gly Trp Thr Gly Ser
 1               5                  10                  15

Leu Leu Gly Asp Arg Glu Glu Ala Ala Arg Pro Arg Leu Leu Pro Leu
            20                  25                  30

Leu Leu Val Leu Leu Gly Cys Leu Gly Leu Gly Val Ala Ala Glu Asp
        35                  40                  45

Ala Glu Val His Ala Glu Asn Trp Leu Arg Leu Tyr Gly Tyr Leu Pro
    50                  55                  60

Gln Pro Ser Arg His Met Ser Thr Met Arg Ser Ala Gln Ile Leu Ala
65                  70                  75                  80

Ser Ala Leu Ala Glu Met Gln Arg Phe Tyr Gly Ile Pro Val Thr Gly
                85                  90                  95

Val Leu Asp Glu Glu Thr Lys Glu Trp Met Lys Arg Pro Arg Cys Gly
            100                 105                 110

Val Pro Asp Gln Phe Gly Val Arg Val Lys Ala Asn Leu Arg Arg Arg
        115                 120                 125

Arg Lys Arg Tyr Ala Leu Thr Gly Arg Lys Trp Asn Asn His His Leu
    130                 135                 140

Thr Phe Ser Ile Gln Asn Tyr Thr Glu Lys Leu Gly Trp Tyr His Ser
145                 150                 155                 160

Met Glu Ala Val Arg Arg Ala Phe Arg Val Trp Glu Gln Ala Thr Pro
                165                 170                 175

Leu Val Phe Gln Glu Val Pro Tyr Glu Asp Ile Arg Leu Arg Arg Gln
            180                 185                 190

Lys Glu Ala Asp Ile Met Val Leu Phe Ala Ser Gly Phe His Gly Asp
        195                 200                 205

Ser Ser Pro Phe Asp Gly Thr Gly Phe Leu Ala His Ala Tyr Phe
    210                 215                 220

Pro Gly Pro Gly Leu Gly Gly Asp Thr His Phe Asp Ala Asp Glu Pro
225                 230                 235                 240

Trp Thr Phe Ser Ser Thr Asp Leu His Gly Asn Asn Leu Phe Leu Val
                245                 250                 255

Ala Val His Glu Leu Gly His Ala Leu Gly Leu Glu His Ser Ser Asn
            260                 265                 270

Pro Asn Ala Ile Met Ala Pro Phe Tyr Gln Trp Lys Asp Val Asp Asn
        275                 280                 285

Phe Lys Leu Pro Glu Asp Asp Leu Arg Gly Ile Gln Gln Leu Tyr Gly
    290                 295                 300

Thr Pro Asp Gly Gln Pro Gln Pro Thr Gln Pro Leu Pro Thr Val Thr
305                 310                 315                 320

Pro Arg Arg Pro Gly Arg Pro Asp His Arg Pro Pro Arg Pro Pro Gln
                325                 330                 335

Pro Pro Pro Pro Gly Gly Lys Pro Glu Arg Pro Pro Lys Pro Gly Pro
            340                 345                 350

Pro Val Gln Pro Arg Ala Thr Glu Arg Pro Asp Gln Tyr Gly Pro Asn
        355                 360                 365

Ile Cys Asp Gly Asp Phe Asp Thr Val Ala Met Leu Arg Gly Glu Met
    370                 375                 380

Phe Val Phe Lys Gly Arg Trp Phe Trp Arg Val Arg His Asn Arg Val
385                 390                 395                 400

Leu Asp Asn Tyr Pro Met Pro Ile Gly His Phe Trp Arg Gly Leu Pro
                405                 410                 415
```

```
Gly Asp Ile Ser Ala Ala Tyr Glu Arg Gln Asp Gly Arg Phe Val Phe
            420                 425                 430

Phe Lys Gly Asp Arg Tyr Trp Leu Phe Arg Glu Ala Asn Leu Glu Pro
            435                 440                 445

Gly Tyr Pro Gln Pro Leu Thr Ser Tyr Gly Leu Gly Ile Pro Tyr Asp
            450                 455                 460

Arg Ile Asp Thr Ala Ile Trp Trp Glu Pro Thr Gly His Thr Phe Phe
465                 470                 475                 480

Phe Gln Glu Asp Arg Tyr Trp Arg Phe Asn Glu Glu Thr Gln Arg Gly
            485                 490                 495

Asp Pro Gly Tyr Pro Lys Pro Ile Ser Val Trp Gln Gly Ile Pro Ala
            500                 505                 510

Ser Pro Lys Gly Ala Phe Leu Ser Asn Asp Ala Ala Tyr Thr Tyr Phe
            515                 520                 525

Tyr Lys Gly Thr Lys Tyr Trp Lys Phe Asp Asn Glu Arg Leu Arg Met
            530                 535                 540

Glu Pro Gly Tyr Pro Lys Ser Ile Leu Arg Asp Phe Met Gly Cys Gln
545                 550                 555                 560

Glu His Val Glu Pro Gly Pro Arg Trp Pro Asp Val Ala Arg Pro Pro
            565                 570                 575

Phe Asn Pro His Gly Gly Ala Glu Pro Gly Ala Asp Ser Ala Glu Gly
            580                 585                 590

Asp Val Gly Asp Gly Asp Gly Asp Phe Gly Ala Gly Val Asn Lys Asp
            595                 600                 605

Gly Gly Ser Arg Val Val Val Gln Met Glu Glu Val Ala Arg Thr Val
            610                 615                 620

Asn Val Val Met Val Leu Val Pro Leu Leu Leu Leu Leu Cys Val Leu
625                 630                 635                 640

Gly Leu Thr Tyr Ala Leu Val Gln Met Gln Arg Lys Gly Ala Pro Arg
            645                 650                 655

Val Leu Leu Tyr Cys Lys Arg Ser Leu Gln Glu Trp Val
            660                 665

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /product= "OTHER"
            /note= "The Xaa at position 5 is Val or Asn."

(xi) SEQUENCE DESCRIPTION: SEQ ID NO:4:

Pro Arg Cys Gly Xaa Pro Asp
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
```

```
            (A) NAME/KEY: Modified-site
            (B) LOCATION: 3
            (D) OTHER INFORMATION: /product= "OTHER"
                /note= "The Xaa at position 3 is Leu, Ile or Phe."

(ix) FEATURE:
            (A) NAME/KEY: Modified-site
            (B) LOCATION: 6
            (D) OTHER INFORMATION: /product= "OTHER"
                /note= "The Xaa at position 6 is Ser, Val or Ala."

(ix) FEATURE:
            (A) NAME/KEY: Modified-site
            (B) LOCATION: 7
            (D) OTHER INFORMATION: /product= "OTHER"
                /note= "The Xaa at position 7 is Leu or Met."

(xi) SEQUENCE DESCRIPTION: SEQ ID NO:5:

His Glu Xaa Gly His Xaa Xaa Gly
1               5

(2) INFORMATION FOR SEQ ID NO:6:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:6:

NNTCTAGACC CAGNTGYGGN RWNCCNGA                                           28

(2) INFORMATION FOR SEQ ID NO:7:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:7:

NNGGATCCCC CAKNSARTGN CCNANYTCRT G                                       31

(2) INFORMATION FOR SEQ ID NO:8:

(i) SEQUENCE CHARACTERISTICS:
            (A) LENGTH: 3456 base pairs
            (B) TYPE: nucleic acid
            (C) STRANDEDNESS: single
            (D) TOPOLOGY: linear (xi) SEQUENCE DESCRIPTION: SEQ ID NO:8:

ACCATTTTGC ATTCCCACAG CAGTGAATGA GAGCTCCTGT TTCTCCACAT TCTCACCAGC        60

ATTTGGTGTT GCTGGTGTTC TGGATTTTGG CCATTCTAAT AGGTGTGTCA TGGTATCTCA       120

TTGTTTTAAT TTGCATTTCT GATGACATAT GAGATGGAGC ATCTTTTCAG ATGCTTATTT       180

GCTGCCTGTG TATCTTCTTT GGTCTTTGGC TCATTTTTTA ATCACGTTGT TTCCTTTTCC       240

TTTCTTTTTT TTGAGAGTCT TGCTCTGTCA TCCGGGGTGG AGTGCAATGG TGCAATCTCA       300

GCCTACTGCA ACCTCTGTCT CCTGGGTTCA AGTGATTCTC CTGCCTCAGC CTCCCAAATA       360

GCTGGCAAAG CTGATGCAGA CACCATGAAG GCCATGAGGC GCCCCGATG TGGTGTTCCA        420

GACAAGTTTG GGCTGAGAT CAAGGCCAAT GTTCGAAGGA AGCGCTACGC CATCCAGGGT       480

CTCAAATGGA ACATAATGA AATCACTTTC TGCATCCAGA ATTACACCCC CAAGGTGGGC       540

GAGTATGCCA CATACGAGGC CATTCGCAAG GCGTTCCGCG TGTGGGAGAG TGCCACACCA       600
```

```
CTGCGCTTCC GCGAGGTGCC CTATGCCTAC ATCCGTGAGG GCCATGAGAA GCAGGCCGAC    660

ATCATGATCT TCTTTGCCGA GGGCTTCCAT GGCGACAGCA CGCCCTTCGA TGGTGAGGGC    720

GGCTTCCTGG CCCATGCCTA CTTCCCAGGC CCCAACATTG GAGGAGACAC CCACTTTGAC    780

TCTGCCGAGC CTTGGACTGT CAGGAATGAG GATCTGAATG GAAATGACAT CTTCCTGGTG    840

GCTGTGCACG AGCTGGGCCA TGCCCTGGGG CTCGAGCATT CCAGTGACCC CTCGGCCATC    900

ATGGCACCCT TTTACCAGTG GATGGACACG GAGAATTTTG TGCTGCCCGA TGATGACCGC    960

CGGGGCATCC AGCAACTTTA TGGGGGTGAG TCAGGGTTCC CCACCAAGAT GCCCCCTCAA   1020

CCCAGGACTA CCTCCCGGCC TTCTGTTCCT GATAAACCCA AAACCCCAC CTATGGGCCC    1080

AACATCTGTG ACGGGAACTT TGACACCGTG GCCATGCTCC GAGGGGAGAT GTTTGTCTTC   1140

AAGGAGCGCT GGTTCTGGCG GGTGAGGAAT AACCAAGTGA TGGATGGATA CCCAATGCCC   1200

ATTGGCCAGT TCTGGCGGGG CCTGCCTGCG TCCATCAACA CTGCCTACGA GAGGAAGGAT   1260

GGCAAATTCG TCTTCTTCAA AGGAGACAAG CATTGGGTGT TTGATGAGGC GTCCCTGGAA   1320

CCTGGCTACC CCAAGCACAT TAAGGAGCTG GGCCGAGGGC TGCCTACCGA CAAGATTGAT   1380

GCTGCTCTCT TCTGGATGCC CAATGGAAAG ACCTACTTCT TCCGTGGAAA CAAGTACTAC   1440

CGTTTCAACG AAGAGCTCAG GGCAGTGGAT AGCGAGTACC CCAAGAACAT CAAAGTCTGG   1500

GAAGGGATCC CTGAGTCTCC CAGAGGGTCA TTCATGGGCA GCGATGAAGT CTTCACTTAC   1560

TTCTACAAGG GGAACAAATA CTGGAAATTC AACAACCAGA AGCTGAAGGT AGAACCGGGC   1620

TACCCCAAGT CAGCCCTGAG GGACTGGATG GGCTGCCCAT CGGGAGGCCG GCCGGATGAG   1680

GGGACTGAGG AGGAGACGGA GGTGATCATC ATTGAGGTGG ACGAGGAGGG CGGCGGGGCG   1740

GTGAGCGCGG CTGCCGTGGT GCTGCCCGTG CTGCTGCTGC TCCTGGTGCT GGCGGTGGGC   1800

CTTGCAGTCT TCTTCTTCAG ACGCCATGGG ACCCCCAGGC GACTGCTCTA CTGCCAGCGT   1860

TCCCTGCTGG ACAAGGTCTG ACGCCCACCG CCGGCCCGCC CACTCCTACC ACAAGGACTT   1920

TGCCTCTGAA GGCCAGTGGC AGCAGGTGGT GGTGGGTGGG CTGCTCCCAT CGTCCCGAGC   1980

CCCCTCCCCG CAGCCTCCTT GCTTCTCTCT GTCCCCTGGC TGGCCTCCTT CACCCTGACC   2040

GCCTCCCTCC CTCCTGCCCC GGCATTGCAT CTTCCCTAGA TAGGTCCCCT GAGGGCTGAG   2100

TGGGAGGGCG GCCCTTTCCA GCCTCTGCCC CTCAGGGGAA CCCTGTAGCT TTGTGTCTGT   2160

CCAGCCCCAT CTGAATGTGT TGGGGGCTCT GCACTTGAAG GCAGGACCCT CAGACCTCGC   2220

TGGTAAAGGT CAAATGGGGT CATCTGCTCC TTTTCCATCC CCTGACATAC CTTAACCTCT   2280

GAACTCTGAC CTCAGGAGGC TCTGGGCACT CCAGCCCTGA AAGCCCCAGG TGTACCCAAT   2340

TGGCAGCCTC TCACTACTCT TTCTGGCTAA AAGGAATCTA ATCTTGTTGA GGGTAGAGAC   2400

CCTGAGACAG TGTGAGGGGG TGGGGACTGC CAAGCCACCC TAAGACCTTG GGAGGAAAAC   2460

TCAGAGAGGG TCTTCGTTGC TCAGTCAGTC AAGTTCCTCG GAGATCTGCC TCTGCCTCAC   2520

CTACCCCAGG GAACTTCCAA GGAAGGAGCC TGAGCCACTG GGGACTAAGT GGGCAGAAGA   2580

AACCCTTGGC AGCCCTGTGC CTCTCGAATG TTAGCCTTGG ATGGGCTTT CACAGTTAGA    2640

AGAGCTGAAA CCAGGGGTGC AGCTGTCAGG TAGGGTGGGG CCGGTGGGAG AGGCCCGGGT   2700

CAGAGCCCTG GGGGTGAGCC TGAAGGCCAC AGAGAAAGAA CCTTGCCCAA ACTCAGGCAG   2760

CTGGGGCTGA GGCCCAAAGG CAGAACAGCC AGAGGGGCA GGAGGGGACC AAAAAGGAAA    2820

ATGAGGACGT GCAGCAGCAT TGGAAGGCTG GGGCCGGGCA GGCCAGGCCA AGCCAAGCAG   2880

GGGGCCACAG GGTGGGCTGT GGAGCTCTCA GGAAGGGCCC TGAGGAAGGC ACACTTGCTC   2940

CTGTTGGTCC CTGTCCTTGC TGCCCAGGCA GCGTGGAGGG GAAGGGTAGG GCAGCCAGAG   3000
```

```
AAAGGAGCAG AGAAGGCACA CAAACGAGGA ATGAGGGGCT TCACGAGAGG CCACAGGGCC    3060

TGGCTGGCCA CGCTGTCCCG GCCTGCTCAC CATCTCAGTG AGGGGCAGGA GCTGGGGCTC    3120

GCTTAGGCTG GGTCCACGCT TCCCTGGTGC CAGCACCCCT CAAGCCTGTC TCACCAGTGG    3180

CCTGCCCTCT CGCTCCCCCA CCCAGCCCAC CCATTGAAGT CTCCTTGGGC CACCAAAGGT    3240

GGTGGCCATG GTACCGGGGA CTTGGGAGAG TGAGACCCAG TGGAGGGAGC AAGAGGAGAG    3300

GGATGTCGGG GGGGTGGGGC ACGGGGTAGG GGAAATGGGG TGAACGGTGC TGGCAGTTCG    3360

GCTAGATTTC TGTCTTGTTT GTTTTTTTGT TTTGTTTAAT GTATATTTTT ATTATAATTA    3420

TTATATATGA ATTCCAAAAA AAAAAAAAAA AAAAA                              3456

(2) INFORMATION FOR SEQ ID NO:9:

(i) SEQUENCE CHARACTERISTICS:
        (A) LENGTH: 3437 base pairs
        (B) TYPE: nucleic acid
        (C) STRANDEDNESS: single
        (D) TOPOLOGY: linear (xi) SEQUENCE DESCRIPTION: SEQ ID NO:9:

AAGTTCAGTG CCTACCGAAG ACAAAGGCGC CCCGAGGGAG TGGCGGTGCG ACCCCAGGGC      60

GTGGGCCCGG CCGCGGAGCC CACACTGCCC GGCTGACCCG GTGGTCTCGG ACCATGTCTC     120

CCGCCCCAAG ACCCCCCCGT TGTCTCCTGC TCCCCCTGCT CACGCTCGGC ACCGCGCTCG     180

CCTCCCTCGG CTCGGCCCAA AGCAGCAGCT TCAGCCCCGA AGCCTGGCTA CAGCAATATG     240

GCTACCTGCC TCCCGGGGAC CTACGTACCC ACACACAGCG CTCACCCCAG TCACTCTCAG     300

CGGCCATCGC TGCCATGCAG AAGTTTTACG GCTTGCAAGT AACAGGCAAA GCTGATGCAG     360

ACACCATGAA GGCCATGAGG CGCCCCCGAT GTGGTGTTCC AGACAAGTTT GGGGCTGAGA     420

TCAAGGCCAA TGTTCGAAGG AAGCGCTACG CCATCCAGGG TCTCAAATGG CAACATAATG     480

AAATCACTTT CTGCATCCAG AATTACACCC CAAGGTGGG CGAGTATGCC ACATACGAGG      540

CCATTCGCAA GGCGTTCCGC GTGTGGGAGA GTGCCACACC ACTGCGCTTC CGCGAGGTGC     600

CCTATGCCTA CATCCGTGAG GGCCATGAGA AGCAGGCCGA CATCATGATC TTCTTTGCCG     660

AGGGCTTCCA TGGCGACAGC ACGCCCTTCG ATGGTGAGGG CGGCTTCCTG GCCCATGCCT     720

ACTTCCCAGG CCCCAACATT GGAGGAGACA CCCACTTTGA CTCTGCCGAG CCTTGGACTG     780

TCAGGAATGA GGATCTGAAT GGAAATGACA TCTTCCTGGT GGCTGTGCAC GAGCTGGGCC     840

ATGCCCTGGG GCTCGAGCAT TCCAGTGACC CCTCGGCCAT CATGGCACCC TTTTACCAGT     900

GGATGGACAC GGAGAATTTT GTGCTGCCCG ATGATGACCG CCGGGGCATC CAGCAACTTT     960

ATGGGGGTGA GTCAGGGTTC CCCACCAAGA TGCCCCCTCA ACCCAGGACT ACCTCCCGGC    1020

CTTCTGTTCC TGATAAACCC AAAAACCCCA CCTATGGGCC CAACATCTGT GACGGGAACT    1080

TTGACACCGT GGCCATGCTC CGAGGGGAGA TGTTTGTCTT CAAGGAGCGC TGGTTCTGGC    1140

GGGTGAGGAA TAACCAAGTG ATGGATGGAT ACCCAATGCC CATTGGCCAG TTCTGGCGGG    1200

GCCTGCCTGC GTCCATCAAC ACTGCCTACG AGAGGAAGGA TGGCAAATTC GTCTTCTTCA    1260

AAGGAGACAA GCATTGGGTG TTTGATGAGG CGTCCCTGGA ACCTGGCTAC CCCAAGCACA    1320

TTAAGGAGCT GGGCCGAGGG CTGCCTACCG ACAAGATTGA TGCTGCTCTC TTCTGGATGC    1380

CCAATGGAAA GACCTACTTC TTCCGTGGAA ACAAGTACTA CCGTTTCAAC GAAGAGCTCA    1440

GGGCAGTGGA TAGCGAGTAC CCCAAGAACA TCAAAGTCTG GGAAGGGATC CCTGAGTCTC    1500

CCAGAGGGTC ATTCATGGGC AGCGATGAAG TCTTCACTTA CTTCTACAAG GGGAACAAAT    1560
```

-continued

```
ACTGGAAATT CAACAACCAG AAGCTGAAGG TAGAACCGGG CTACCCCAAG TCAGCCCTGA    1620

GGGACTGGAT GGGCTGCCCA TCGGGAGGCC GGCCGGATGA GGGGACTGAG GAGGAGACGG    1680

AGGTGATCAT CATTGAGGTG GACGAGGAGG GCGGCGGGGC GGTGAGCGCG GCTGCCGTGG    1740

TGCTGCCCGT GCTGCTGCTG CTCCTGGTGC TGGCGGTGGG CCTTGCAGTC TTCTTCTTCA    1800

GACGCCATGG GACCCCCAGG CGACTGCTCT ACTGCCAGCG TTCCCTGCTG ACAAGGTCT     1860

GACGCCCACC GCCGGCCCGC CCACTCCTAC CACAAGGACT TTGCCTCTGA AGGCCAGTGG    1920

CAGCAGGTGG TGGTGGGTGG GCTGCTCCCA TCGTCCCGAG CCCCCTCCCC GCAGCCTCCT    1980

TGCTTCTCTC TGTCCCCTGG CTGGCCTCCT TCACCCTGAC CGCCTCCCTC CCTCCTGCCC    2040

CGGCATTGCA TCTTCCCTAG ATAGGTCCCC TGAGGGCTGA GTGGGAGGGC GGCCCTTTCC    2100

AGCCTCTGCC CCTCAGGGGA ACCCTGTAGC TTTGTGTCTG TCCAGCCCCA TCTGAATGTG    2160

TTGGGGGCTC TGCACTTGAA GGCAGGACCC TCAGACCTCG CTGGTAAAGG TCAAATGGGG    2220

TCATCTGCTC CTTTTCCATC CCCTGACATA CCTTAACCTC TGAACTCTGA CCTCAGGAGG    2280

CTCTGGGCAC TCCAGCCCTG AAAGCCCCAG GTGTACCCAA TTGGCAGCCT CTCACTACTC    2340

TTTCTGGCTA AAAGGAATCT AATCTTGTTG AGGGTAGAGA CCCTGAGACA GTGTGAGGGG    2400

GTGGGGACTG CCAAGCCACC CTAAGACCTT GGGAGGAAAA CTCAGAGAGG GTCTTCGTTG    2460

CTCAGTCAGT CAAGTTCCTC GGAGATCTGC CTCTGCCTCA CCTACCCCAG GGAACTTCCA    2520

AGGAAGGAGC CTGAGCCACT GGGGACTAAG TGGGCAGAAG AAACCCTTGG CAGCCCTGTG    2580

CCTCTCGAAT GTTAGCCTTG GATGGGGCTT TCACAGTTAG AAGAGCTGAA ACCAGGGGTG    2640

CAGCTGTCAG GTAGGGTGGG GCCGGTGGGA GAGGCCCGGG TCAGAGCCCT GGGGGTGAGC    2700

CTGAAGGCCA CAGAGAAAGA ACCTTGCCCA AACTCAGGCA GCTGGGGCTG AGGCCCAAAG    2760

GCAGAACAGC CAGAGGGGGC AGGAGGGGAC CAAAAAGGAA AATGAGGACG TGCAGCAGCA    2820

TTGGAAGGCT GGGGCCGGGC AGGCCAGGCC AAGCCAAGCA GGGGGCCACA GGGTGGGCTG    2880

TGGAGCTCTC AGGAAGGGCC CTGAGGAAGG CACACTTGCT CCTGTTGGTC CCTGTCCTTG    2940

CTGCCCAGGC AGCGTGGAGG GGAAGGGTAG GGCAGCCAGA GAAAGGAGCA GAGAAGGCAC    3000

ACAAACGAGG AATGAGGGGC TTCACGAGAG GCCACAGGGC CTGGCTGGCC ACGCTGTCCC    3060

GGCCTGCTCA CCATCTCAGT GAGGGGCAGG AGCTGGGGCT CGCTTAGGCT GGGTCCACGC    3120

TTCCCTGGTG CCAGCACCCC TCAAGCCTGT CTCACCAGTG GCCTGCCCTC TCGCTCCCCC    3180

ACCCAGCCCA CCCATTGAAG TCTCCTTGGG CCACCAAAGG TGGTGGCCAT GGTACCGGGG    3240

ACTTGGGAGA GTGAGACCCA GTGGAGGGAG CAAGAGGAGA GGGATGTCGG GGGGGTGGGG    3300

CACGGGGTAG GGGAAATGGG GTGAACGGTG CTGGCAGTTC GGCTAGATTT CTGTCTTGTT    3360

TGTTTTTTTG TTTTGTTTAA TGTATATTTT TATTATAATT ATTATATATG AATTCCAAAA    3420

AAAAAAAAAA AAAAAA                                                   3437
```

(2) INFORMATION FOR SEQ ID NO:10:

(i) SEQUENCE CHARACTERISTICS:
        (A) LENGTH: 3530 base pairs
        (B) TYPE: nucleic acid
        (C) STRANDEDNESS: single
        (D) TOPOLOGY: linear (xi) SEQUENCE DESCRIPTION: SEQ ID NO:10:

```
GCGAGGATCC GGCGTGCAGT GTTCCGAGCT GGGCTGGGCG CCGAGAGCAT GGGCAGCGAC      60

CCGAGCGCGC CCGGACGGCC GGGCTGGACG GGCAGCCTCC TCGGCGACCG GGAGGAGGCG     120
```

```
GCGCGGCCGC GACTGCTGCC GCTGCTCCTG GTGCTTCTGG GCTGCCTGGG CCTTGGCGTA      180

GCGGCCGAAG ACGCGGAGGT CCATGCCGAG AACTGGCTGC GGCTTTATGG CTACCTGCCT      240

CAGCCCAGCC GCCATATGTC CACCATGCGT TCCGCCCAGA TCTTGGCCTC GGCCCTTGCA      300

GAGATGCAGC GCTTCTACGG GATCCCAGTC ACCGGTGTGC TCGACGAAGA GACCAAGGAG      360

TGGATGAAGC GGCCCCGCTG TGGGGTGCCA GACCAGTTCG GGGTACGAGT GAAAGCCAAC      420

CTGCGGCGGC GTCGGAAGCG CTACGCCCTC ACCGGGAGGA AGTGGAACAA CCACCATCTG      480

ACCTTTAGCA TCCAGAACTA CACGGAGAAG TTGGGCTGGT ACCACTCGAT GGAGGCGGTG      540

CGCAGGGCCT TCCGCGTGTG GGAGCAGGCC ACGCCCTGG TCTTCCAGGA GGTGCCCTAT       600

GAGGACATCC GGCTGCGGCG ACAGAAGGAG GCCGACATCA TGGTACTCTT TGCCTCTGGC      660

TTCCACGGCG ACAGCTCGCC GTTTGATGGC ACCGGTGGCT TTCTGGCCCA CGCCTATTTC      720

CCTGGCCCCG GCCTAGGCGG GGACACCCAT TTTGACGCAG ATGAGCCCTG GACCTTCTCC      780

AGCACTGACC TGCATGGAAA CAACCTCTTC CTGGTGGCAG TGCATGAGCT GGGCCACGCG      840

CTGGGGCTGG AGCACTCCAG CAACCCCAAT GCCATCATGG CGCCGTTCTA CCAGTGGAAG      900

GACGTTGACA ACTTCAAGCT GCCCGAGGAC GATCTCCGTG GCATCCAGCA GCTCTACGGT      960

ACCCCAGACG GTCAGCCACA GCCTACCCAG CCTCTCCCCA CTGTGACGCC ACGGCGGCCA     1020

GGCCGGCCTG ACCACCGGCC GCCCCGGCCT CCCCAGCCAC CACCCCCAGG TGGGAAGCCA     1080

GAGCGGCCCC CAAAGCCGGG CCCCCCAGTC CAGCCCCGAG CCACAGAGCG GCCCGACCAG     1140

TATGGCCCCA ACATCTGCGA CGGGGACTTT GACACAGTGG CCATGCTTCG CGGGGAGATG     1200

TTCGTGTTCA AGGGCCGCTG GTTCTGGCGA GTCCGGCACA ACCGCGTCCT GGACAACTAT     1260

CCCATGCCCA TCGGGCACTT CTGGCGTGGT CTGCCCGGTG ACATCAGTGC TGCCTACGAG     1320

CGCCAAGACG GTCGTTTTGT CTTTTTCAAA GGTGACCGCT ACTGGCTCTT TCGAGAAGCG     1380

AACCTGGAGC CCGGCTACCC ACAGCCGCTG ACCAGCTATG GCCTGGGCAT CCCCTATGAC     1440

CGCATTGACA CGGCCATCTG GTGGGAGCCC ACAGGCCACA CCTTCTTCTT CCAAGAGGAC     1500

AGGTACTGGC GCTTCAACGA GGAGACACAG CGTGGAGACC CTGGGTACCC CAAGCCCATC     1560

AGTGTCTGGC AGGGGATCCC TGCCTCCCCT AAAGGGGCCT TCCTGAGCAA TGACGCAGCC     1620

TACACCTACT TCTACAAGGG CACCAAATAC TGGAAATTCG ACAATGAGCG CCTGCGGATG     1680

GAGCCCGGCT ACCCCAAGTC CATCCTGCGC GACTTCATGG GCTGCCAGGA GCACGTGGAG     1740

CCAGGCCCCC GATGGCCCGA CGTGGCCCGG CCGCCCTTCA ACCCCCACGG GGGTGCAGAG     1800

CCCGGGGCGG ACAGCGCAGA GGGCGACGTG GGGGATGGGG ATGGGGACTT TGGGGCCGGG     1860

GTCAACAAGG ACGGGGCAG CCGCGTGGTG GTGCAGATGG AGGAGGTGGC ACGGACGGTG      1920

AACGTGGTGA TGGTGCTGGT GCCACTGCTG CTGCTGCTCT GCGTCCTGGG CCTCACCTAC     1980

GCGCTGGTGC AGATGCAGCG CAAGGGTGCG CCACGTGTCC TGCTTTACTG CAAGCGCTCG     2040

CTGCAGGAGT GGGTCTGACC ACCCAGCGCT CCTGCTAACG GTGCTCAGGG GGCGCCTGTG     2100

GTTCTGAGAT GGCTCCCAGG GGCTCCCTCC GCCCCCAGGT AGGGGCCCCT CTCAGCCCTC     2160

ACACACCCTG TCTGCCCCGC CCTCATTATT TATGTCCAGG TGTTTGTTTT GTTTTGTTTT     2220

TGGCACCTTA CTTGACCATT TGTTTCTGTT TCCCCGACTG GGGCAGGGTG TTTAGAATTT     2280

TCTAAATGTA GTTCTGCTCC AGACAGGGAA TTAGGCCCCC ATCATCCTCT GGCTTGGCCA     2340

CAGCCAGGGG AGCAGAGGGG CAGAGGCCCA CATTGGAAGA GCAGCACCTC CTCAGCCTGA     2400

ACCCCAGGGC TGTAACTGCC AGGCTCTCTT TGCCCAGTTG GAGACTGTCT GGCCCCCCTG     2460
```

```
GTCCCCTCCT TCCCAAGTGA GTCTCTCTGG GCCTTAGGAA GAGCCTTCCA CCCAGGGGCA    2520

GCCCCAGGCC AAAGGGGACC TGGAAGGGAG GTGGGCCGTG GCCCTTGAGT CCCCATTGAG    2580

GCTTGGTTCC TTCCCAATCC AGTGGACTTC GCAGTCCACT TCTGACAGCC TCAGTGACCC    2640

TGGCTCCTTG TGCCAGAGAA CCCAGCCCAC CCCCGGCAGC AGCCCCCAGC TCCCACCTCC    2700

CCTTGGGCCC ACACCTTCTT CCCTCTCTGG AGAAAGGGCC CTGGGCCTGC CTCACCACGG    2760

ACCAAAGGGA GTCTGCCAGG GCCCCTCTCC CCAGGGAAGC AGCAGCCTCG CCCCTGGCAG    2820

AGATGCCTCC CTGAGCTAGA ACCCTCTGTT CCTTCCCTGT GCCTCCTCCC TCCCTCCCGA    2880

CTCACACCAC TAGCCTCAGG GGTCTGAGCT CCAGCTCCTT TGGGCTTCAG CTGCCAGTGT    2940

CCTGAGCCCC AGGGAGAGGG GGCTGGTGGG TGCCTAGGCC TGGGCAGTGG ATGGCCGTGA    3000

ATGGGTGCCC ACAGTGTCAG GCACTGGGCA TGAGGGGTTC CTCCCCTCCA GCTCCCTGTG    3060

CCCCCAGGGT CCTGGGAGGA GAGACACTGG TGGGGATAGG CCAGCCGCGC ATCAGACTGT    3120

GAACCCCACG AAGGAGCCCA TTGTGGCCTA AGAGGCTGCC CTCCTGTGCT CAGCCCTGAG    3180

GACAGATGCC TCCTTCCTCT TTTCCTTCCC AAAGCAAGCA AGAGGCCGTG GCTGCTGTGG    3240

GAAATGGTAC TGTACAGCTG GCTCTACTTC CCCATGGCCC TGAGCGAGTG GAGTCTGCCA    3300

CCCAGGATCC CCAAGGCACT TGAGGGGGAA GGATTCTGCT GGCCTCTGCG AGTGGTTTCT    3360

TGTGCACTGG CACCAAGTGC GGGTCCGGCA GCTTCTGCCC CCTGCAGAAC CGGAGAGCCA    3420

GCTAAGGGGT GGGGCTGCGG GGGTTCCGTG TCCACCCCCA TACATTTATT TCTGTAAATA    3480

ATGTGCACTG AATAAATTGT ACAGCCGGCA AAAAAAAAAA AAAAAAAAA              3530

(2) INFORMATION FOR SEQ ID NO:11:

(i) SEQUENCE CHARACTERISTICS:
         (A) LENGTH: 7 amino acids
         (B) TYPE: amino acid
         (C) STRANDEDNESS: single
         (D) TOPOLOGY: linear (xi) SEQUENCE DESCRIPTION: SEQ ID NO:11:

Pro Arg Cys Gly Val Pro Asp
1               5

(2) INFORMATION FOR SEQ ID NO:12:

(i) SEQUENCE CHARACTERISTICS:
         (A) LENGTH: 6 amino acids
         (B) TYPE: amino acid
         (C) STRANDEDNESS: single
         (D) TOPOLOGY: linear (xi) SEQUENCE DESCRIPTION: SEQ ID NO:12:

Arg Arg Lys Arg Tyr Ala
1               5

(2) INFORMATION FOR SEQ ID NO:13:

(i) SEQUENCE CHARACTERISTICS:
         (A) LENGTH: 11 amino acids
         (B) TYPE: amino acid
         (C) STRANDEDNESS: single
         (D) TOPOLOGY: linear (xi) SEQUENCE DESCRIPTION: SEQ ID NO:13:

His Glu Leu Gly His Ala Leu Gly Leu Glu His
1               5                   10
```

(2) INFORMATION FOR SEQ ID NO:14:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:14:

```
TCTAGACCCA GGTGCGGGGT GCCGGACAAG TTTGGGGCTG AGATCAAGGC CAATGTTCGA      60

AGGAAGCGCT ACGCCATCCA GGGTCTCAAA TGGCAACATA ATGAAATCAC TTTCTGCATC     120

CAGAATTACG CGCCCAAGGT GGGCGAGTAT GCCACATACG AGGCCATTCG CAAGGCGTTC     180

CGCATGTGGG AGAGTGCCAC ACCACTGCGC TTGCGCGAGG TGCCCTATGC CTACATCCGT     240

GAGGCCATGA GAAGCAGGCC GACATCATGA TCTTCTTTGC CGAGGGTTCC ATGGCGACAG     300

CGCCCTTCGA TGGTGAGGGC GGCTTCCTGG CCCGTGCCTA CTTCCCAGGC CCCAACATTG     360

GAGGAGACAC CCACTTTGAC TCTGCCGAGC CTTGGACTGT CAGGAATGAG GATCTGAATG     420

GAAATACATC TTCCTGGTGG CTGTGCACGA ACTCGGCCAC CGCTGGGGAT CC             472
```

(2) INFORMATION FOR SEQ ID NO:15:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (xi) SEQUENCE DESCRIPTION: SEQ ID NO:15:

```
TCTAGACCCA GGTGCGGGAA GCCGGACCAG TTCGGGGTAC GAGTGAAAGC CAACCTGCGG      60

CGGCGTCGGA AGCGCTACGC CCTCACCGGG AGGAAGTGGA ATAACCAACC ATCTGACCTT     120

TAGCATCCAG AACTACACCG GAGAAGTTGG GCTGGTACCA CTCGATGGAG GCGGTGCGCA     180

GGGCCTTCCG CGTGTGGGAG CAGGCCACGC CCCTGGTCTT CCAGGAGGTG CCCTATGAGA     240

CATCCGGCTG CGGCGACAGA AGGAGGCCGA CATCATGGTA CTCTTTCCCT CTGGCTTCCA     300

CGGCGAACAG CTCGCCGTTT GATGGCACCG GTGGCTTTCT GGCCCACGCC TATTTCCCTG     360

GCCCCGGCCT AGGCGGGGAC ACCCATTTTG ACGCAGATGA GCCCTGGACC TTCTCCAGCA     420

CTGACCTGCA TGGAAACAAC CTCTTCCTGG TGGCAGTGCA TGAGCTGGGC CACGCGCTGG     480

GGGATCC                                                               487
```

(2) INFORMATION FOR SEQ ID NO:16:

(i) SEQUENCE CHARACTERISTICS:
        (A) LENGTH: 469 amino acids
        (B) TYPE: amino acid
        (C) STRANDEDNESS: single
        (D) TOPOLOGY: linear (xi) SEQUENCE DESCRIPTION: SEQ ID NO:16:

```
Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
            35                  40                  45

Arg Gln Val Glu Lys Arg Arg Asn Ser Gly Pro Val Val Glu Lys Leu
        50                  55                  60

Lys Gln Met Gln Glu Phe Phe Gly Leu Lys Val Thr Gly Lys Pro Asp
```

```
                65                  70                  75                  80
Ala Glu Thr Leu Lys Val Met Lys Gln Pro Arg Cys Gly Val Pro Asp
                        85                  90                  95

Val Ala Gln Phe Val Leu Thr Glu Gly Asn Pro Arg Trp Glu Gln Thr
                100                 105                 110

His Leu Thr Tyr Arg Ile Glu Asn Tyr Thr Pro Asp Leu Pro Arg Ala
                115                 120                 125

Asp Val Asp His Ala Ile Glu Lys Ala Phe Gln Leu Trp Ser Asn Val
            130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
                180                 185                 190

Gly Asp Ala His Phe Asp Glu His Glu Arg Trp Thr Asn Asn Phe Thr
            195                 200                 205

Glu Tyr Asn Leu His Arg Val Ala Ala His Glu Leu Gly His Ser Leu
        210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
                260                 265                 270

Gln Thr Pro Lys Ala Cys Asp Ser Lys Leu Thr Phe Asp Ala Ile Thr
                275                 280                 285

Thr Ile Arg Gly Glu Val Met Phe Phe Lys Asp Arg Phe Tyr Met Arg
        290                 295                 300

Thr Asn Pro Phe Tyr Pro Glu Val Glu Leu Asn Phe Thr Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
            355                 360                 365

Gly Phe Pro Arg Thr Val Lys His Ile Asp Ala Ala Leu Ser Glu Glu
370                 375                 380

Asn Thr Gly Lys Thr Tyr Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
                420                 425                 430

Asp Gly Phe Phe Tyr Phe Phe His Gly Thr Arg Gln Tyr Lys Phe Asp
            435                 440                 445

Pro Lys Thr Lys Arg Ile Leu Thr Leu Gln Lys Ala Asn Ser Trp Phe
        450                 455                 460

Asn Cys Arg Lys Asn
465
```

(2) INFORMATION FOR SEQ ID NO:17:

(i) SEQUENCE CHARACTERISTICS:
    (A) LENGTH: 466 amino acids
    (B) TYPE: amino acid
    (C) STRANDEDNESS: single
    (D) TOPOLOGY: linear (xi) SEQUENCE DESCRIPTION: SEQ ID NO:17:

```
Met Phe Ser Leu Lys Thr Leu Pro Phe Leu Leu Leu His Val Gln
 1               5                  10                  15

Ile Ser Lys Ala Phe Pro Val Ser Ser Lys Glu Lys Asn Thr Lys Thr
                 20                  25                  30

Val Gln Asp Tyr Leu Glu Lys Phe Tyr Gln Leu Pro Ser Asn Gln Tyr
                 35                  40                  45

Gln Ser Thr Arg Lys Asn Gly Thr Asn Val Ile Val Glu Lys Leu Lys
 50                  55                  60

Glu Met Gln Arg Phe Phe Gly Leu Asn Val Thr Gly Lys Pro Asn Glu
 65                  70                  75                  80

Glu Thr Leu Asp Met Met Lys Lys Pro Arg Cys Gly Val Pro Asp Ser
                 85                  90                  95

Gly Gly Phe Met Leu Thr Pro Gly Asn Pro Lys Trp Glu Arg Thr Asn
                100                 105                 110

Leu Thr Tyr Arg Ile Arg Asn Tyr Thr Pro Gln Leu Ser Glu Ala Glu
            115                 120                 125

Val Glu Arg Ala Ile Lys Asp Ala Phe Glu Leu Trp Ser Val Ala Ser
130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175

Asn Gly Ile Leu Ala His Ala Phe Gln Pro Gly Gln Gly Ile Gly Gly
                180                 185                 190

Asp Ala His Phe Asp Ala Glu Glu Thr Trp Thr Asn Thr Ser Ala Asn
                195                 200                 205

Tyr Asn Leu Phe Leu Val Ala Ala His Glu Phe Gly His Ser Leu Gly
            210                 215                 220

Leu Ala His Ser Ser Asp Pro Gly Ala Leu Met Tyr Pro Asn Tyr Ala
225                 230                 235                 240

Phe Arg Glu Thr Ser Asn Tyr Ser Leu Pro Gln Asp Asp Ile Asp Gly
                245                 250                 255

Ile Gln Ala Ile Tyr Gly Leu Ser Ser Asn Pro Ile Gln Pro Thr Gly
                260                 265                 270

Pro Ser Thr Pro Lys Pro Cys Asp Pro Ser Leu Thr Phe Asp Ala Ile
                275                 280                 285

Thr Thr Leu Arg Gly Glu Ile Leu Phe Phe Lys Asp Arg Tyr Phe Trp
290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
                340                 345                 350

Ser Gly Tyr Asp Ile Leu Gln Gly Tyr Pro Lys Asp Ile Ser Asn Tyr
                355                 360                 365

Gly Phe Pro Ser Ser Val Gln Ala Ile Asp Ala Ala Val Phe Tyr Arg
```

```
                    370                 375                 380
Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415

Phe Pro Gly Ile Glu Ser Lys Asp Ala Val Phe Gln Gln Glu His Phe
            420                 425                 430

Phe His Val Phe Ser Gly Pro Arg Tyr Tyr Ala Phe Asp Leu Ile Ala
        435                 440                 445

Gln Arg Val Thr Arg Val Ala Arg Gly Asn Lys Trp Leu Asn Cys Arg
            450                 455                 460

Tyr Gly
465

(2) INFORMATION FOR SEQ ID NO:18:

(i) SEQUENCE CHARACTERISTICS:
        (A) LENGTH: 660 amino acids
        (B) TYPE: amino acid
        (C) STRANDEDNESS: single
        (D) TOPOLOGY: linear (xi) SEQUENCE DESCRIPTION: SEQ ID NO:18:

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Phe Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
50                  55                  60

Cys Asn Leu Phe Val Leu Lys Asp Thr Leu Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
                100                 105                 110

Phe Pro Arg Lys Pro Lys Trp Asp Lys Asn Gln Ile Thr Tyr Arg Ile
            115                 120                 125

Ile Gly Tyr Thr Pro Asp Leu Asp Pro Glu Thr Val Asp Asp Ala Phe
        130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190

His Ala Phe Ala Pro Gly Thr Gly Val Gly Gly Asp Ser His Phe Asp
            195                 200                 205

Asp Asp Glu Leu Trp Thr Leu Gly Glu Gly Gln Val Val Arg Val Lys
        210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255
```

```
Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
            275                 280                 285

Gln Pro Cys Lys Phe Pro Phe Arg Phe Gln Gly Thr Ser Tyr Asp Ser
            290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Thr Ala Asn Tyr Asp Asp Asp
            370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
            450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
            515                 520                 525

Glu Glu Lys Ala Val Phe Phe Ala Gly Asn Glu Tyr Trp Ile Tyr Ser
            530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
            610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660
```

-continued (2) INFORMATION FOR SEQ ID NO:19:

(i) SEQUENCE CHARACTERISTICS:
        (A) LENGTH: 707 amino acids
        (B) TYPE: amino acid
        (C) STRANDEDNESS: single
        (D) TOPOLOGY: linear (xi) SEQUENCE DESCRIPTION: SEQ ID NO:19:

```
Met Ser Leu Trp Gln Pro Val Leu Val Leu Leu Val Leu Gly Cys
 1               5                  10                  15

Cys Phe Ala Ala Pro Arg Gln Arg Gln Ser Thr Leu Val Leu Phe Pro
                 20                  25                  30

Gly Asp Leu Arg Thr Asn Leu Thr Asp Arg Gln Leu Ala Glu Glu Tyr
             35                  40                  45

Leu Tyr Arg Tyr Gly Tyr Thr Arg Val Ala Glu Met Arg Gly Glu Ser
 50                  55                  60

Lys Ser Leu Gly Pro Ala Leu Leu Leu Leu Gln Lys Gln Leu Ser Leu
 65                  70                  75                  80

Pro Glu Thr Gly Glu Leu Asp Ser Ala Thr Leu Lys Ala Met Arg Thr
                 85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
             115                 120                 125

Ser Glu Asp Leu Pro Arg Ala Val Ile Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
            275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
            355                 360                 365
```

-continued

```
Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705
```

(2) INFORMATION FOR SEQ ID NO:20:

(i) SEQUENCE CHARACTERISTICS:
        (A) LENGTH: 477 amino acids
        (B) TYPE: amino acid
        (C) STRANDEDNESS: single
        (D) TOPOLOGY: linear (xi) SEQUENCE DESCRIPTION: SEQ ID NO:20:

```
Met Lys Ser Leu Pro Ile Leu Leu Leu Leu Cys Val Ala Val Cys Ser
1               5                   10                  15
```

```
Ala Tyr Pro Leu Asp Gly Ala Ala Arg Gly Glu Asp Thr Ser Met Asn
             20                  25                  30

Leu Val Gln Lys Tyr Leu Glu Asn Tyr Asp Leu Glu Lys Asp Val
         35                  40                  45

Lys Gln Phe Val Arg Arg Lys Asp Ser Gly Pro Val Val Lys Lys Ile
         50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                 85                  90                  95

Val Gly His Phe Arg Thr Phe Pro Gly Ile Pro Lys Trp Arg Lys Thr
                100                 105                 110

His Leu Thr Tyr Arg Ile Val Asn Tyr Thr Pro Asp Leu Pro Lys Asp
                115                 120                 125

Ala Val Asp Ser Ala Val Glu Lys Ala Leu Lys Val Trp Glu Glu Val
            130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
                180                 185                 190

Gly Asp Ala His Phe Asp Asp Asp Glu Gln Trp Thr Lys Asp Thr Thr
            195                 200                 205

Gly Thr Asn Leu Phe Leu Val Ala Ala His Glu Ile Gly His Ser Leu
        210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Asp Ser Pro Glu Thr
                260                 265                 270

Pro Leu Val Pro Thr Glu Pro Val Pro Pro Glu Pro Gly Thr Pro Ala
        275                 280                 285

Asn Cys Asp Pro Ala Leu Ser Phe Asp Ala Val Ser Thr Leu Arg Gly
        290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
        370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
            420                 425                 430
```

-continued

```
Ile Asp Ser Lys Ile Asp Ala Val Phe Glu Glu Phe Gly Phe Phe Tyr
        435                 440                 445

Phe Phe Thr Gly Ser Ser Gln Leu Glu Phe Asp Pro Asn Ala Lys Lys
        450                 455                 460

Val Thr His Thr Leu Lys Ser Asn Ser Trp Leu Asn Cys
465                 470                 475
```

(2) INFORMATION FOR SEQ ID NO:21:

(i) SEQUENCE CHARACTERISTICS:
        (A) LENGTH: 476 amino acids
        (B) TYPE: amino acid
        (C) STRANDEDNESS: single
        (D) TOPOLOGY: linear (xi) SEQUENCE DESCRIPTION: SEQ ID NO:21:

```
Met Met His Leu Ala Phe Leu Val Leu Leu Cys Leu Pro Val Cys Ser
1               5                   10                  15

Ala Tyr Pro Leu Ser Gly Ala Ala Lys Glu Glu Asp Ser Asn Lys Asp
                20                  25                  30

Leu Ala Gln Gln Tyr Leu Glu Lys Tyr Tyr Asn Leu Glu Lys Asp Val
            35                  40                  45

Lys Gln Phe Arg Arg Lys Asp Ser Asn Leu Ile Val Lys Lys Ile Gln
        50                  55                  60

Gly Met Gln Lys Phe Leu Gly Leu Glu Val Thr Gly Lys Leu Asp Thr
65                  70                  75                  80

Asp Thr Leu Glu Val Met Arg Lys Pro Arg Cys Gly Val Pro Asp Val
                85                  90                  95

Gly His Phe Ser Ser Phe Pro Gly Met Pro Lys Trp Arg Lys Thr His
                100                 105                 110

Leu Thr Tyr Arg Ile Val Asn Tyr Thr Pro Asp Leu Pro Arg Asp Ala
            115                 120                 125

Val Asp Ser Ala Ile Glu Lys Ala Leu Lys Val Trp Glu Glu Val Thr
        130                 135                 140

Pro Leu Thr Phe Ser Arg Leu Tyr Glu Gly Ala Asp Ile Met Ile
145                 150                 155                 160

Ser Phe Ala Val Lys Glu His Gly Asp Phe Tyr Ser Phe Asp Gly Pro
                165                 170                 175

Gly His Ser Leu Ala His Ala Tyr Pro Pro Gly Pro Gly Leu Tyr Gly
                180                 185                 190

Asp Ile His Phe Asp Asp Asp Glu Lys Trp Thr Glu Asp Ala Ser Gly
            195                 200                 205

Thr Asn Leu Phe Leu Val Ala Ala His Glu Leu Gly His Ser Leu Gly
        210                 215                 220

Leu Phe His Ser Ala Asn Thr Glu Ala Leu Met Tyr Pro Leu Tyr Asn
225                 230                 235                 240

Ser Phe Thr Glu Leu Ala Gln Phe Arg Leu Ser Gln Asp Asp Val Asn
                245                 250                 255

Gly Ile Gln Ser Leu Tyr Gly Pro Pro Ala Ser Thr Glu Glu Pro
                260                 265                 270

Leu Val Pro Thr Lys Ser Val Pro Ser Gly Ser Glu Met Pro Ala Lys
            275                 280                 285

Cys Asp Pro Ala Leu Ser Phe Asp Ala Ile Ser Thr Leu Arg Gly Glu
        290                 295                 300

Tyr Leu Phe Phe Lys Asp Arg Tyr Phe Trp Arg Arg Ser His Trp Asn
305                 310                 315                 320
```

```
Pro Glu Pro Glu Phe His Leu Ile Ser Ala Phe Trp Pro Ser Leu Pro
                325                 330                 335

Ser Tyr Leu Asp Ala Ala Tyr Glu Val Asn Ser Arg Asp Thr Val Phe
            340                 345                 350

Ile Phe Lys Gly Asn Glu Phe Trp Ala Ile Arg Gly Asn Glu Val Gln
            355                 360                 365

Ala Gly Tyr Pro Arg Gly Ile His Thr Leu Gly Phe Pro Pro Thr Ile
        370                 375                 380

Arg Lys Ile Asp Ala Ala Val Ser Asp Lys Glu Lys Lys Lys Thr Tyr
385                 390                 395                 400

Phe Phe Ala Ala Asp Lys Tyr Trp Arg Phe Asp Glu Asn Ser Gln Ser
                405                 410                 415

Met Glu Gln Gly Phe Pro Arg Leu Ile Ala Asp Asp Phe Pro Gly Val
            420                 425                 430

Glu Pro Lys Val Asp Ala Val Leu Gln Ala Phe Gly Phe Phe Tyr Phe
            435                 440                 445

Phe Ser Gly Ser Ser Gln Phe Glu Phe Asp Pro Asn Ala Arg Met Val
        450                 455                 460

Thr His Ile Leu Lys Ser Asn Ser Trp Leu His Cys
465                 470                 475

(2) INFORMATION FOR SEQ ID NO:22:

(i) SEQUENCE CHARACTERISTICS:
        (A) LENGTH: 488 amino acids
        (B) TYPE: amino acid
        (C) STRANDEDNESS: single
        (D) TOPOLOGY: linear (xi) SEQUENCE DESCRIPTION: SEQ ID NO:22:

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
                100                 105                 110

Arg Ile Leu Arg Phe Pro Trp Gln Leu Val Gln Glu Gln Val Arg Gln
            115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                 155                 160

Arg Tyr Trp Asp Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
```

-continued

```
                195                 200                 205
Leu Leu Gln Val Ala Ala His Glu Phe Gly His Val Leu Gly Leu Gln
    210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
                260                 265                 270

Pro Gln Ala Gly Ile Asp Thr Asn Glu Ile Ala Pro Leu Glu Pro Asp
            275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
                340                 345                 350

His Ile Trp Phe Phe Gln Gly Ala Gln Tyr Trp Val Tyr Asp Gly Glu
                355                 360                 365

Lys Pro Val Leu Gly Pro Ala Pro Leu Thr Glu Leu Gly Leu Val Arg
    370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Arg Ala Thr Asp Trp Arg Gly Val
                420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
    450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485
```